US010839973B2

(12) United States Patent
Muehlhauser et al.

(10) Patent No.: US 10,839,973 B2
(45) Date of Patent: Nov. 17, 2020

(54) X-RAY TUBE AND GAMMA SOURCE FOCAL SPOT TUNING APPARATUS AND METHOD

(71) Applicant: Illinois Tool Works Inc., Glenview, IL (US)

(72) Inventors: Brett A. Muehlhauser, Rogers, MN (US); Matthew J. Johnson, Rogers, MN (US); Tucker J. Behrns, Rogers, MN (US)

(73) Assignee: Illinois Tool Works Inc., Glenview, IL (US)

( * ) Notice: Subject to any disclaimer, the term of this patent is extended or adjusted under 35 U.S.C. 154(b) by 79 days.

(21) Appl. No.: 16/079,049

(22) PCT Filed: Feb. 23, 2017

(86) PCT No.: PCT/US2017/019174
§ 371 (c)(1),
(2) Date: Aug. 22, 2018

(87) PCT Pub. No.: WO2017/147320
PCT Pub. Date: Aug. 31, 2017

(65) Prior Publication Data
US 2019/0051424 A1 Feb. 14, 2019

Related U.S. Application Data

(60) Provisional application No. 62/299,888, filed on Feb. 25, 2016.

(51) Int. Cl.
*G21K 1/02* (2006.01)
*A61B 6/00* (2006.01)
*A61N 5/10* (2006.01)

(52) U.S. Cl.
CPC ............ *G21K 1/025* (2013.01); *A61B 6/4291* (2013.01); *A61N 2005/1089* (2013.01)

(58) Field of Classification Search
CPC .................. G21K 1/025; A61B 6/4291; A61N 2005/1089
(Continued)

(56) References Cited

U.S. PATENT DOCUMENTS 4,672,648 A 6/1987 Mattson et al.
5,231,654 A 7/1993 Kwasnick et al.
(Continued)

FOREIGN PATENT DOCUMENTS

DE 10047366 A1 5/2002
JP 2005241381 A 9/2005
(Continued)

OTHER PUBLICATIONS

International Search Report and Written Opinion of International Application No. PCT/US2017/019174, dated Sep. 26, 2017, 26 pp.
(Continued)

*Primary Examiner* — David P Porta
*Assistant Examiner* — Gisselle M Gutierrez
(74) *Attorney, Agent, or Firm* — Shumaker & Sieffert, P.A.

(57) ABSTRACT

An apparatus (112) provides for tuning of an effective focal spot size of a radiation source. The apparatus may comprise a plurality of inter-channel structures (214) defining a plurality of channels (216) passing through the apparatus from a first surface (218) to a second surface (220). The inter-channel structures comprise a first substance and the channels contains a second substance. The first substance attenuates radiation more than the second substance. The inter-channel structures may define the channels such that lines passing through the channels converge at a location on or near the surface of a focal spot (212).

22 Claims, 16 Drawing Sheets

(58) Field of Classification Search
USPC .......................................................... 378/145
See application file for complete search history.

(56) References Cited

U.S. PATENT DOCUMENTS

| | | | | |
|---|---|---|---|---|
| 5,303,459 | A * | 4/1994 | Kurakake | ............... G21K 1/025 |
| | | | | 29/407.05 |
| 5,644,614 | A * | 7/1997 | Toth | ....................... A61B 6/032 |
| | | | | 378/145 |
| 6,353,227 | B1 | 3/2002 | Boxen | |
| 2002/0015474 | A1 * | 2/2002 | Tybinkowski | ......... G21K 1/025 |
| | | | | 378/153 |
| 2008/0095320 | A1 * | 4/2008 | Kanack | .................. G21K 1/025 |
| | | | | 378/149 |
| 2008/0170664 | A1 | 7/2008 | Kalman | |
| 2012/0321041 | A1 | 12/2012 | Ikhlef et al. | |
| 2012/0328076 | A1 * | 12/2012 | Ikhlef | ..................... G21K 1/025 |
| | | | | 378/62 |
| 2014/0105361 | A1 * | 4/2014 | Vogtmeier | ............... G21K 1/10 |
| | | | | 378/62 |
| 2014/0112451 | A1 | 4/2014 | Figueroa Saavedra et al. | |
| 2016/0045767 | A1 * | 2/2016 | Bender | ................ A61N 5/1045 |
| | | | | 378/149 |
| 2016/0320322 | A1 * | 11/2016 | Suzuki | ..................... G21K 1/04 |
| 2019/0290224 | A1 * | 9/2019 | Clark | ..................... G21K 1/025 |

FOREIGN PATENT DOCUMENTS

| | | |
|---|---|---|
| JP | 2012181111 A | 9/2012 |
| JP | 2013195407 A | 9/2013 |
| JP | 2014124305 A | 7/2014 |
| WO | 2014131173 A1 | 9/2014 |

OTHER PUBLICATIONS

Invitation to Pay Additional Fees from International Application No. PCT/US2017/019174, dated Jun. 7, 2017, 18 pp.
International Preliminary Report on Patentability from International Application No. PCT/US2017/019174, dated Sep. 7, 2018, 15 pp.

* cited by examiner

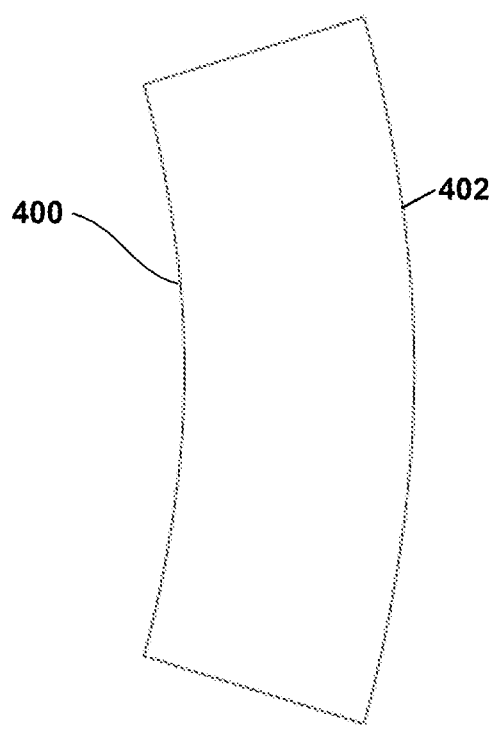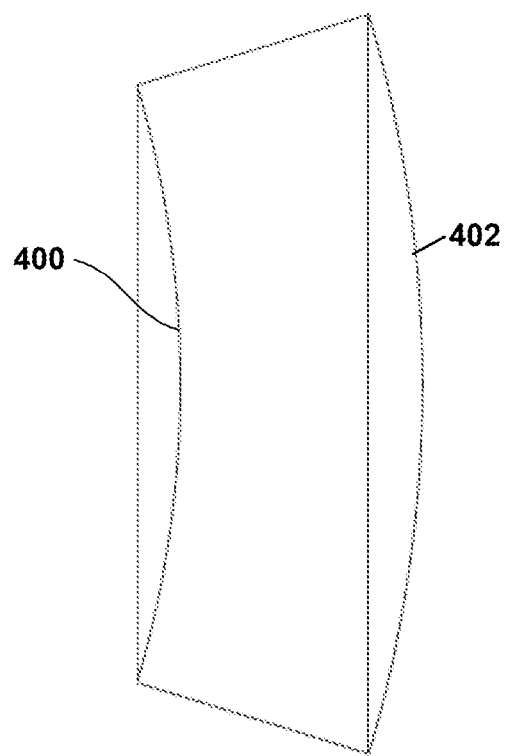
FIG. 12　　　　　FIG. 13

X-RAY TUBE AND GAMMA SOURCE FOCAL SPOT TUNING APPARATUS AND METHOD

TECHNICAL FIELD

This disclosure relates to apparatuses and methods for use in x-ray and gamma-ray imaging.

BACKGROUND

An x-ray tube is an apparatus that emits x-ray radiation. In many instances, an x-ray tube comprises a vacuum tube that encloses a cathode and an anode. The cathode emits electrons and the anode collects the emitted electrons. A voltage between the cathode and anode accelerates the electrons across a gap from the cathode to the anode. When the electrons strike the anode, x-rays are emitted. The stream of electrons flowing from the cathode to the anode may be referred to as an electron beam or simply a beam.

The x-rays generated when electrons strike the anode pass through the vacuum tube and may be detected by an x-ray detector. Objects lying in the path of the x-rays may attenuate the x-rays. Thus, the x-ray detector detects fewer x-rays at locations of greater attenuation and more x-rays at locations of less attenuations. The pattern of attenuation forms an x-ray image.

The electron beam is not a 1-dimensional line from the cathode to the anode. Rather, the electrons are emitted from a 2- or 3-dimensional area on the cathode and strike a 2- or 3-dimensional area of the anode. Because the electron beam strikes a 2- or 3-dimensional area of the anode, the x-rays are emitted from the 2- or 3-dimensional area instead of a single 0-dimensional point.

Ideally, x-rays would be emitted from a single 0-dimensional point. This would ensure that no portion of the x-ray detector falls within a penumbra. A penumbra occurs when an object obscures part of a light source, but not another part of the light source. For instance, just as a penumbra occurs during an eclipse when the moon obscures part of the sun, penumbras can occur when objects attenuate x-rays from non-point sources. Penumbras cause distortions in x-ray images, often producing a negative impact on image quality that worsens with an increase in the area from which x-rays are emitted and when a subject is positioned closer to the non-point source.

Accordingly, attempts have been made to minimize the area from which x-rays are emitted. In general, such attempts focus the electron beam on a small area of the anode. The small area struck by the electron beam, and from which x-rays are emitted, may be referred to as the "focal spot" of the anode or the "focal spot" of the radiation source. Focusing all the energy of the electron beam at a very small spot can damage the anode (e.g., by overheating that spot on the anode). Accordingly, to achieve a small focal spot, and thereby reduce penumbras, the energy of the electron beam must be reduced. As a result, the x-ray flux output of the x-ray tube is reduced. This reduction in x-ray flux may limit the applications of an x-ray tube with a small focal spot. For example, it may not be practical to use an x-ray tube with a small focal spot for radiography of some objects with high attenuation due to the reduction in x-ray flux causing an increase in exposure time.

Although the discussion above referred to x-rays, the same principles apply for other types of radiation, such as gamma rays.

SUMMARY

In general, this disclosure describes apparatuses and methods for use in x-ray and gamma ray imaging. For ease of explanation, much of this disclosure refers to x-rays when other types of radiation, such as gamma rays or rays in other spectral bands of electromagnetic radiation, may be equally applicable. As described herein, an apparatus is disposed between an x-ray tube and an object to be inspected. For example, the apparatus may be disposed at a port of the x-ray tube. The apparatus has a source-side surface and an object-side surface. The source-side surface faces the x-ray tube and the object-side surface faces the object to be inspected. Furthermore, the apparatus comprises a series of column structures that define channels through the apparatus from the source-side surface to the object-side surface. The channels may be filled with one or more low-attenuation substances, such as air, a polymer, a carbon based material or other lower-attenuation substances. The column structures may be made of, or comprise, one or more higher-attenuation substances, such as tungsten, lead, lead glass, or tantalum. Thus, x-rays may pass through the channels without significant attenuation, but may not pass through the column structures without significant attenuation.

The apparatus may provide the effect of changing or tuning the effective size of the focal spot without modifying the x-ray tube itself. For instance, the apparatus may provide the effect of a smaller focal spot size without the focal spot actually being smaller. The apparatus may provide this effect by blocking x-ray photons emitted by outer portions of the actual focal spot, while allowing x-ray photons from a central area of the actual focal spot to pass through the apparatus. To achieve this effect, the channels of the apparatus are defined such that the channels are aligned throughout their courses with the paths of x-ray photons emitted by the central area of the actual focal spot. Thus, x-ray photons emitted from the central area of the actual focal spot may pass through the apparatus while x-ray photons emitted from non-central areas of the actual focal spot are attenuated by the high-attenuation substances of the column structures of the apparatus.

In one example, this disclosure describes an apparatus for tuning an effective focal spot size of a radiation source, the apparatus comprising: a plurality of inter-channel structures defining a plurality of channels passing through the apparatus from a first surface to a second surface, the inter-channel structures comprising a first substance, the channels containing a second substance, the first substance attenuating radiation more than the second substance, the inter-channel structures defining the channels such that lines passing through the channels converge.

In another example, this disclosure describes a method of tuning an effective focal spot of a radiation source, the method comprising: positioning an apparatus between the radiation source and a radiation detector, the apparatus comprising a plurality of inter-channel structures defining a plurality of channels passing through the apparatus from a first surface to a second surface, the inter-channel structures comprising a first substance, the channels containing a second substance, the first substance attenuating radiation more than the second substance, the inter-channel structures defining the channels such that lines passing through the channels converge; and activating an electron beam that travels across a gap from a cathode to an anode, wherein an area covered by a projection of the lines through the channels is smaller than a focal spot of the electron beam on the anode.

In another example, this disclosure describes a system comprising: a radiation source configured to deliver radiation towards an object; a radiation detector configured to detect the radiation; and an apparatus for tuning an effective focal spot size of the radiation source, the apparatus comprising: a plurality of inter-channel structures defining a plurality of channels passing through the apparatus from a first surface to a second surface, wherein the inter-channel structures comprise a first substance, the channels include a second substance, the first substance attenuates the radiation more than the second substance, and the inter-channel structures define the channels such that lines passing through the channels converge.

The details of one or more examples are set forth in the accompanying drawings and the description below. Other features, objects, and advantages will be apparent from the description, drawings, and claims.

BRIEF DESCRIPTION OF DRAWINGS

FIG. 12 is a conceptual diagram illustrating an example profile view of a focal spot tuning apparatus, in accordance with one or more techniques of this disclosure.

FIG. 13 is a conceptual diagram illustrating another example profile view of a focal spot tuning apparatus, in accordance with one or more techniques of this disclosure.

DETAILED DESCRIPTION

Figure 1:
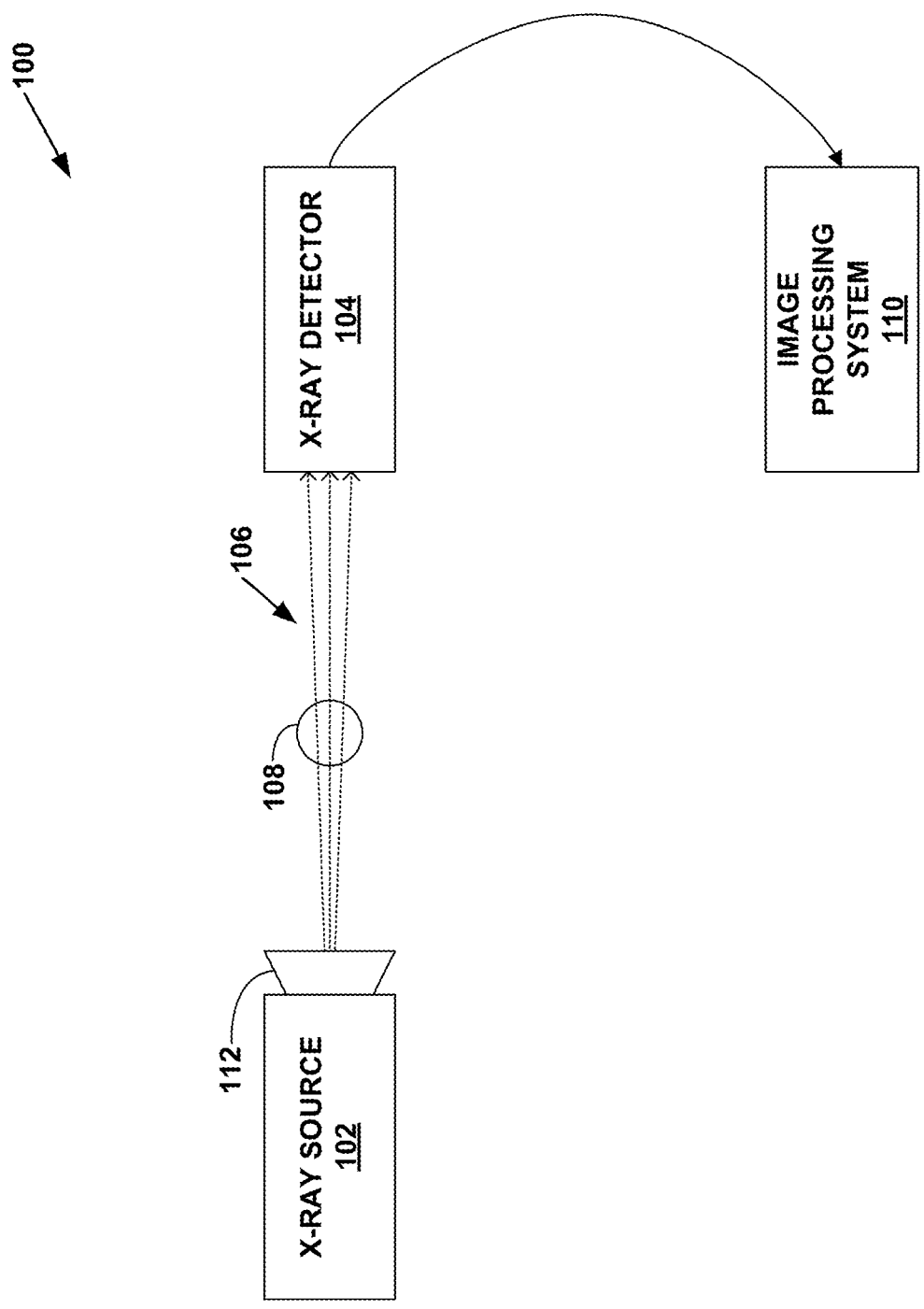
FIG. 1 is a block diagram illustrating an example x-ray inspection apparatus that may perform one or more techniques of this disclosure.

FIG. 1 is a block diagram illustrating an example x-ray inspection apparatus 100 that may perform one or more techniques of this disclosure. In the example of FIG. 1, apparatus 100 includes an x-ray source 102 and an x-ray detector 104. X-ray source 102 emits x-rays 106. X-ray source 102 may be an example of an x-ray tube. As shown in the example of FIG. 1, x-rays 106 may emerge from x-ray source 102 following divergent paths. X-ray detector 104 detects x-rays, such that those emitted by x-ray source 102. Although FIG. 1 and the remainder of this disclosure primarily discusses x-rays, the discussion of x-rays may be applicable to other types of radiation, such as gamma rays. Hence, x-ray source 102 may be an example of a radiation source and x-ray detector 104 may be an example of a radiation detector.

Furthermore, in the example of FIG. 1, a target object 108 is disposed between x-ray source 102 and x-ray detector 104. Target object 108 may be the object under investigation. For example, target object 108 may be a piece of industrial equipment that is being inspected for defects. As x-rays 106 pass through target object 108, particular structures within target object 108 may attenuate x-rays 106 more than other structures within target object 108. As a result, x-ray detector 104 detects less x-ray radiation at locations on x-ray detector 104 corresponding to ray lines from x-ray source 102 through the higher attenuation structures within target object 108. Thus, the higher-attenuation structures cast x-ray shadows on x-ray detector 104.

In some examples, x-ray detector 104 comprises an x-ray sensitive film that can be developed to generate a physical radiograph that reveals patterns of shadows cast by the higher-attenuation structures within target object 108. In other examples, x-ray detector 104 may generate signals, such as electrical or optical signals, representative of the patterns of shadows. In such examples, an image processing system 110 may process the signals to generate an electronic/digital radiograph that reveals the patterns of shadows. Image processing system 110 may comprise a computing device, such as a personal computer, specialized computing device, or another type of computing device.

In various examples, x-ray detector 104 is implemented in various ways. For example, x-ray detector 104 may include a flat panel x-ray detector (FPD). In other examples, x-ray detector 104 may include a lens-coupled scintillation detector, a linear diode array (LDA), or another type of x-ray detector. A FPD may include a layer of scintillation material, such as Cesium Iodide fabricated on amorphous silicon on a glass detector array. The scintillator layer absorbs x-rays and emits visible light photons that are, in turn, detected by a solid state detector. The detector pixel size may range from tens to hundreds of micrometers. In some examples where x-ray detector 104 comprises a flat-panel x-ray detector. In some examples, the pixel size of x-ray detector 104 may be in the range of 25 micrometers to 400 micrometers. Furthermore, the field of view of common commercial FPDs may range from approximately 100 mm to 500 mm. Commercial FPDs may be used in applications requiring large fields of view.

High-resolution applications may use lens-coupled detectors that use an optical lens to relay emitted visible light to a detector, such as a charge-coupled device (CCD) or a complementary metal-oxide-semiconductor (CMOS) detector. In some examples, the lens may provide magnification in the range of 1× to 100×, thus making the effective pixel size between 0.1 to 20 micrometers. In some examples where x-ray detector 104 comprises a lens-coupled detector, the pixel size of x-ray detector 104 is in a range of 0.1 micrometers to 10 micrometers. Furthermore, in some examples where x-ray detector 104 comprises a lens-coupled detector, the field of view may range from 0.2 mm to 25 mm.

As shown in the example of FIG. 1, a focal spot tuning apparatus 112 is disposed between x-ray source 102 and target object 108. In some examples, focal spot tuning apparatus 112 is mounted onto or within x-ray source 102. In some examples, focal spot tuning apparatus 112 forms an integral part of another component of x-ray source 102, such as a shielding material of x-ray source 102. In some examples, focal spot tuning apparatus 112 is movable, removable, and/or replaceable. As described in greater detail below, focal spot tuning apparatus 112 may provide the effect of changing or tuning an effective size of a focal spot of an x-ray tube of x-ray source 102 without modifying the x-ray tube itself.

As described in detail below, focal spot tuning apparatus 112 may tune the effective focal spot of an x-ray tube or gamma ray source while removing scatter radiation being emitted from the x-ray tube or gamma ray source. Focal spot tuning apparatus 112 may comprise a grid-like structure defining a plurality of channels comprising air or substantially low attenuation materials adjacent to inter-channel structures that comprise a substantially high attenuation material. In some examples, focal spot tuning apparatus 112 may provide a motion mechanism for further tuning the effective focal spot of the electron beam, as well as removing fixed image grid patterns. A method for aligning focal spot tuning apparatus 112 for optimization of beam output is also provided. Use of focal spot tuning apparatus 112 may improve the spatial resolution and contrast sensitivity of images produced with a given x-ray tube or gamma-ray source.

Focal spot tuning apparatus 112 may be applied in various settings. For instance, focal spot tuning apparatus 112 may be applied to x-ray and gamma-ray systems used in the industrial, medical, and other industries both in fixed positioned equipment and portable equipment. Furthermore, focal spot tuning apparatus 112 can be used with static anode tubes as well as rotating anode tubes and can be employed with sealed tubes as well as with open vacuum tubes.

Figure 2:
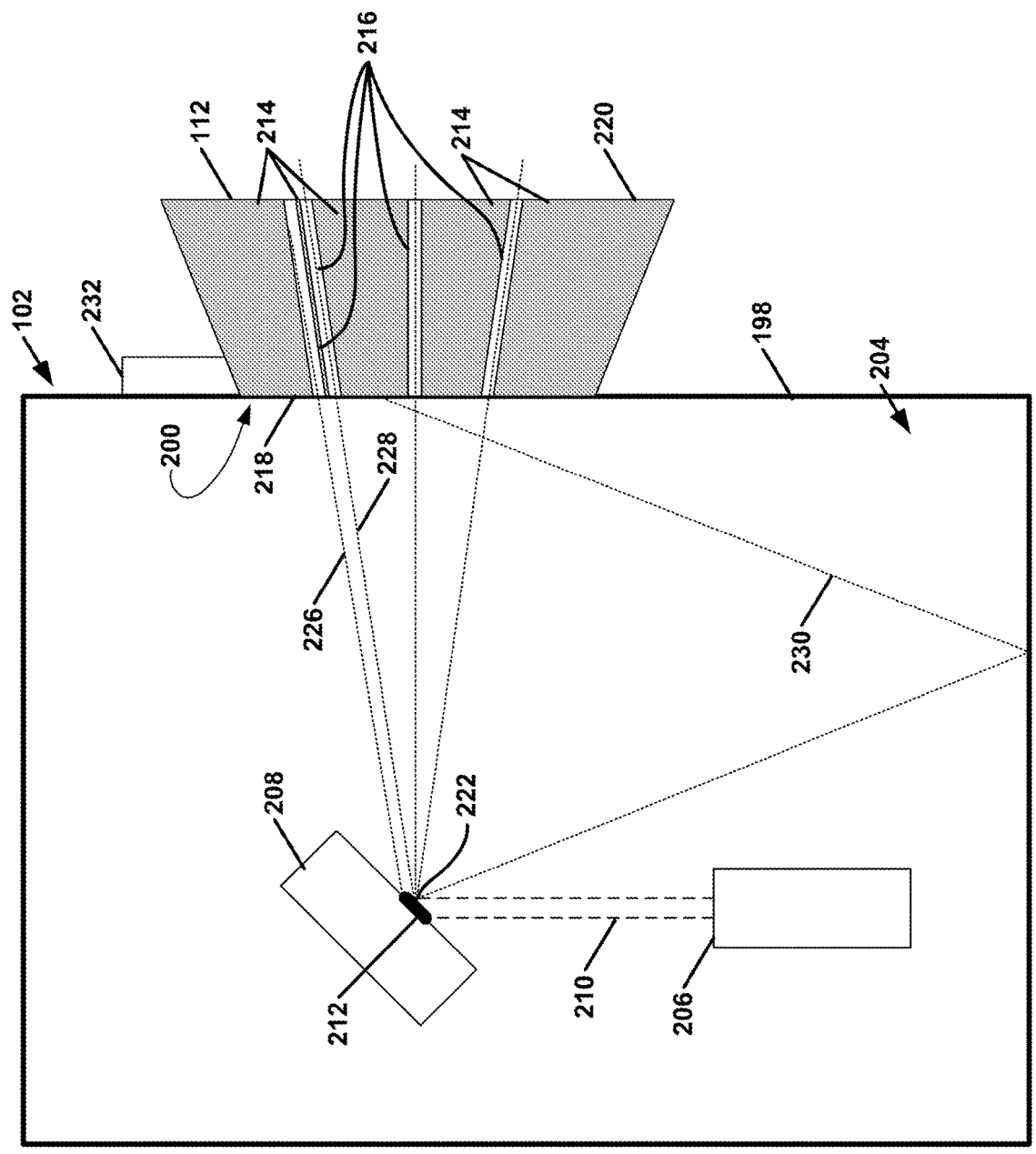
FIG. 2 is a conceptual diagram illustrating an example x-ray source with a focal spot tuning apparatus, in accordance with one or more techniques of this disclosure.

FIG. 2 is a conceptual diagram illustrating an example of x-ray source 102 with focal spot tuning apparatus 112, in accordance with one or more techniques of this disclosure. FIG. 2 is provided for purposes of explanation only and is not intended to show scale or realistic shapes of components.

In the example of FIG. 2, x-ray source 102 comprises housing 198. Housing 198 may comprise a shielding material to block x-rays from emanating from x-ray source 102 in undesired places. Housing 198 may be constructed of various materials, such as steel, lead, tungsten, tantalum, or other metals or materials. Although steel, lead, tantalum, or tungsten may be useful in housing 198 for shielding x-rays, other materials may also work for housing 198, particularly if gamma rays or other bands of electromagnetic radiation are used instead of x-rays from an x-ray source. For instance, housing 198 may comprise a metal ceramic tube. Housing 198 defines an enclosed interior space 204. Interior space 204 may be substantially evacuated, such that a vacuum is present in interior space 204 of housing 198. Interior space 204 of housing 198 contains a cathode 206 and an anode 208. Cathode 206 may also be referred to herein as a filament. Cathode 206 emits a beam of electrons 210 (dashed lines) and anode 208 collects the emitted electrons. This disclosure also refers to beam of electrons 210 as electron beam 210. When the electrons of electron beam 210 strike anode 208, x-rays (lines of small dots) are emitted by anode 208.

A window 200 (i.e., beam port) of lower attenuation material is defined in housing 198 to allow emission of x-rays from the interior of x-ray source 102. In the example of FIG. 2, window 200 is aligned with focal spot tuning apparatus 112.

As shown in the example of FIG. 2, electrons of electron beam 210 strike a multi-dimensional area of anode 208, referred to in this disclosure as focal spot 212. In the application of a conventional focal spot tube (i.e., an x-ray tube with a focal spot>400 μm), a mini-focus x-ray tube (between 100 μm and 400 μm) and gamma-ray sources, geometric magnification is substantially limited by the size of focal spot (the point of origin of the rays). Indications of a measurement of a size of a focal spot (e.g., 400 μm) in this disclosure refer to measurements of a focal spot as defined by the manufacturer, such as the longest dimension of the focal spot. As described elsewhere in the disclosure, because focal spot 212 is not a single geometric point, penumbras may occur in radiographs. Thus, when using one of these common tube designs (e.g., conventional or mini-focus) or a gamma ray source, geometric magnification may be limited by geometric unsharpness (e.g., penumbra) due to the focal spot size.

Conventional configurations of x-ray tubes may control the focal spots by various techniques, such as controlling electron emitter filament size, focusing of the electron beam, cropping and/or collimating the electron beam, adjusting the angle of the target (e.g., anode 208) where the electron beam strikes the target and any combination of the aforementioned techniques. Some X-ray tubes continuously defocus the electron beam with an increase of tube wattage. Additionally, "variable focus" tubes can adjust the focusing of the electron beam incrementally to generate multiple focal spots. Furthermore, some x-ray tubes are equipped with multiple filaments, often of different sizes, to generate multiple focal spots from a single x-ray tube. Gamma ray sources come in various sizes which is the primary factor for defining their focal spot size.

In the example of FIG. 2, focal spot tuning apparatus 112 is disposed primarily outside housing 198 of x-ray source 102. However, in other examples, focal spot tuning apparatus 112 may be primarily or completely inside housing 198. Focal spot tuning apparatus 112 comprises a set of column structures 214. Column structures 214 define channels 216 through focal spot tuning apparatus 112 from a source-side surface 218 of focal spot tuning apparatus 112 to an object-side surface 220 of focal spot tuning apparatus 112. Accordingly, column structures 214 may be referred to as inter-channel structures. For the sake of simplicity, the example of FIG. 2 only shows four channels. However, column structures 214 may define many more channels, which may be spaced and arranged in a regular or random pattern.

Channels 216 may be filled with a substance having relatively low attenuation for x-rays. For example, channels 216 may contain with air or another substance. However, column structures 214 may be made of a substance having relatively high attenuation for x-rays. For example, column structures 214 may be made of a high-density material, such as tungsten, lead, lead glass, or tantalum. Because channels 216 contain a low-attenuation substance while column structures 214 comprise a high-attenuation substance, x-rays may be able to pass through channels 216 and may be attenuated by column structures 214.

Column structures 214 define channels 216 such that channels 216 are angled inward from object-side surface 220 to source-side surface 218 such that conceptual lines passing through the centerlines of channels 216 also pass through an area within focal spot 212. Thus, the conceptual lines may converge at a location on or near (e.g., behind) a surface of focal spot 212. This disclosure may refer to the area within focal spot 212 as effective focal spot 222. Thus, effective focal spot 222 may be a sub-region of focal spot 212. In other words, an area covered by a projection of the channels is smaller than a focal spot of the electron beam on the anode.

Because of the angles of channels 216, x-rays emitted by portions of focal spot 212 outside effective focal spot 222 are less likely to pass through channels 216 from source-side surface 218 to object-side surface 220 without being attenuated by column structures 214. For instance, x-ray 226 is emitted by a portion of focal spot 212 outside effective focal spot 222 while x-ray 228 is emitted from within effective focal spot 222 at the same angle. As shown in the example of FIG. 2, x-ray 228 is able to pass through one of channels 216 without significant attenuation while x-ray 226 cannot. Thus, the x-rays emerging from object-side surface 220 of focal spot tuning apparatus 112 are primarily emitted from within effective focal spot 222 while x-rays emitted from outside effective focal spots 222 are substantially blocked.

Different focal spot tuning apparatuses may be used to achieve differently sized effective focal spots. For instance, a smaller effective focal spot can be achieved with a particular focal spot tuning apparatus when conceptual lines passing through channels defined by the particular focal spot tuning apparatus intersect a smaller area of focal spot 212. Thus, the size of the effective focal spot can be a function of the angles of the channels, the lengths of the channels, and the distance of the focal spot tuning apparatus from focal spot 212. Hence, by substituting different focal spot tuning apparatuses used with x-ray source 102, a user may be able to tune the effective size of focal spot 212. In other words, using focal spot tuning apparatus 112, the effective focal spot of x-ray source 102 can be tuned by a combination of the size of the collimation openings (i.e., the openings of channels 216), the divergence angle of the collimation openings and column structures 214 and their points of origin size.

Thus, focal spot tuning apparatus 112 may enable changing or tuning the focal spot size of an existing x-ray tube or gamma source external to the device itself without any modification to the internal design or operation of the tube or source. Various configurations of focal spot tuning apparatus 112 may provide effective focal spots that are smaller than the manufacturer's specified focal spot, thus expanding the geometric magnification capabilities of conventional and mini-focus x-ray tubes, as well as gamma ray sources. As previously discussed, focal spot tuning apparatus 112 may reduce penumbra by using cropping of the undesirable x-ray photons coming from the outer portion of the standard focal spot (e.g., focal spot 212). The virtual (effective) focal spot can be adjusted by using focal spot tuning apparatus 112 to change the beam cone size and divergence angle to a smaller or larger point of origin up to the original manufacturer's focal spot size. The grid structure of focal spot tuning apparatus 112 can be fabricated to match various desired beam cone sizes and angles. In general, a desired focal spot size is matched to the grid's column size and depth and the beam divergence angle and point of origin size to produce a beam representing the characteristics of the desired focal spot. The virtual focal spot (e.g., effective focal spot 222) may be reduced with a smaller column size, a larger column depth and/or thickness, and a steeper beam collimation divergence angle having a smaller center point of the collimation structure. Additionally, the virtual focal spot may be reduced by positioning focal spot tuning apparatus 112 closer to focal spot 212. The opposite can be achieved for a larger effective focal spot. Focal spot tuning apparatuses designed for use close to focal spot 212 may have more severe channel angles. For instance, a focal spot tuning apparatus positioned with a ½ inch gap between the source-side surface of the focal spot tuning apparatus and window 200 and another focal spot tuning apparatus positioned with a ⅛-inch gap between the source-side surface of the focal spot tuning apparatus with a more severe column angle may net a smaller virtual focal spot. Moving a focal spot tuning apparatus closer to window 200 without changing the column angle may also reduce the virtual focal spot size. Motion system 232 may be configured to move the apparatus toward or away from an anode of the radiation source to adjust the effective focal spot size.

Additionally, some x-rays emitted from focal spot 212 are scattered off surfaces within x-ray source 102, such as housing 198. That is, it is understood that x-ray tubes and gamma sources generate scatter radiation from within the x-ray tubes and gamma sources, shielding, camera, and near a beam port of the x-ray tubes. For instance, in the example of FIG. 2, x-ray 230 is scattered off housing 198. Scattered x-rays may reduce contrast in radiographs. Additionally, image sharpness can be negatively impacted by this scatter radiation when geometric magnification is applied. Because scattered x-rays may arrive at source-side surface 218 of focal spot tuning apparatus 112 at random angles, most scattered x-rays will not pass cleanly through channels 216 but will instead be attenuated by column structures 214. Hence, the design of focal spot tuning apparatus 112 may provide continuous multi-port collimation of an x-ray beam, attenuating much of the scatter radiation coming from inside interior space 204 (e.g., a vacuum chamber) of x-ray source 102, as well as scatter radiation external to interior space 204 of x-ray source 102 or source coming from the surfaces of the beam port, the outer shielding and the outer casing of x-ray source 102. Thus, focal spot tuning apparatus 112 may have the added benefit of increasing contrast and sharpness in radiographs by reducing the effect of scattered x-rays.

Column structures 214 may attenuate some x-rays emitted from within effective focal spot 222. Thus, focal spot tuning apparatus 112 itself may cast a shadow on x-ray detector 104. For example, if column structures 214 define a grid pattern of channels, the grid pattern may appear within the radiographs. To counter this, a motion system 232 may be configured to move focal spot tuning apparatus 112 such that column structures 214 do not continuously cast shadows at the same locations on x-ray detector 104. For instance, motion system 232 may be configured to rotate focal spot tuning apparatus 112. Thus, motion can be used to assist in the removal of fixed patterning within an image, as well as for further focal spot tuning. In some examples, fixed patterning within an image can also be removed through common subtraction methods. In such subtraction methods, pixel values corresponding to areas blocked by focal spot tuning apparatus 112 may have relatively low luminance values. Accordingly, to compensate, values may be subtracted from such pixel values, or such pixel values may be otherwise adjusted. Where motion of focal spot tuning apparatus 112 is desired, the motion can be provided with mechanical, electrical, acoustic, magnetic, piezoelectric, pneumatic and hydraulic methods, including but not limited to rotation, nutation, and oscillation. In portable applications, the motion of focal spot tuning apparatus 112 may employ a battery or other power source, as well as mechanical-only drive mechanisms such as spring tension, pneumatic and hydraulic motion generating systems. In the example of FIG. 2, motion system 232 is located outside housing 198. In other examples, motion system 232 is located inside housing 198 or partially within and partially outside housing 198.

The effective focal spot may be further adjustable with the focal spot tuning apparatus 112 by providing motion to the device with a variable offset displacement as defined by the desired focal spot and the size of the collimation openings. For instance, a mechanism may angularly cant or tilt focal spot tuning apparatus 112 (with or without manipulation) to produce even further focal spot reduction for a specific opening spacing size. In other words, the mechanism may cant or tilt focal spot tuning apparatus 112 to adjust the effective focal spot size. As indicated elsewhere in this disclosure, changing the position of focal spot tuning apparatus 112 relative to the actual focal spot may change the size of the effective focal spot.

The openings of channels 216 may be defined by focal spot tuning apparatus 112 to have various shapes. For instance, focal spot tuning apparatus 112 may define the openings of channels 216 (or column structures 214) to have round, square, triangular, hexagonal, or other geometrical shapes or combinations of geometrical shapes to potentially optimize shielding to opening pattern. The pattern of openings of channels 216 or pattern of column structures 214 can vary in alignment to one another to provide optimum opening to column structure ratio for different motion configurations and image fixed pattern reduction. For instance, the hole and/or wall size may vary through the thickness of the apparatus. In one example, column structures 214 may define the openings of channels 216 at source-side surface 218 to be wider than the openings of channels 216 at object-side surface 220, or vice versa. In more general terms, column structures 214 may define the openings of channels 216 at a first surface of focal spot tuning apparatus 112 to be wider than the openings of channels 216 at a second surface of focal spot tuning apparatus 112. The outer, object-side surface 220 of focal spot tuning apparatus 112 may be circular, square or another geometry to optimize implementation with a given tube/source design as well as to optimize the beam output for a given detector size and/or shape. Focal spot tuning apparatus 112 can be used in conjunction with further beam cropping/blocking collimation for reduced field of view applications, further removing tube/source scatter as well as scatter producing primary beam photons.

In some examples, focal spot tuning apparatus 112 can further be produced with multiple layers of different collimation opening configurations to provide further adjustment of effective focal spot 222. Furthermore, for higher energy applications, the thickness/depth of focal spot tuning apparatus 112 may be increased, as well as the thickness of the shielding column structures 214 to provide further attenuation of the undesirable higher energy x-ray photons.

As discussed elsewhere in this disclosure, as electron beam 210 is focused onto a smaller area of anode 208, the voltage that can be applied across the gap between cathode 206 and anode 208 decreases. This is because, if the voltage remained constant, the energy imparted by electron beam 210 to each square unit of surface area of anode 208 would increase. Receiving too much energy in a small area can damage anode 208. Accordingly, as the size of focal spot 212 decreases, the voltage, and therefore wattage, may be forced to decrease. As the voltage decreases, the x-ray flux output of anode 208 decreases. In this context, flux refers to the radiant energy emitted per unit time.

Thus, it is understood that micro-focus tube (e.g., x-ray tubes with focal spots less than 100 µm) designs are typically limited in wattage and therefore cannot generate the x-ray flux output of mini-focus (focal spots between 100 µm and 400 µm) and conventional focal spot tubes (focal spots greater than 400 µm). Focal spot tuning apparatus 112 may enable a conventional x-ray tube (e.g., with the wattage of a conventional x-ray tube) to produce focal spots ranging from conventional, mini-focus and micro-focus, thus significantly increasing the effective use of the x-ray tube through a wider range of geometric magnification applications while retaining the ability to function in high wattage applications. Additionally, some micro-focus tubes are significantly more expensive and often less stable than mini-focus and conventional focus tubes for production applications. This is often due to their open vacuum design and the additional components supporting the open vacuum design. This may be especially true in open vacuum design microfocus tubes above 225 kv. Thus, use of focal spot tuning apparatus 112 may provide the effect of a micro-focus or mini-focus tube without the significant cost increases of actual micro-focus or mini-focus tubes.

Furthermore, it is understood that many x-ray tubes have varying x-ray photon intensity across different locations of the focal spot. Focal spot tuning apparatus 112 may enable selection of a smaller "hot spot" region of a larger focal spot to provide the optimal position of highest x-ray flux output for the reduced focal spot area. This may also provide a more consistent focal spot shape and output intensity. Single focal spot and multi-focal spot tubes can be used in conjunction with this device. In the case of multi-focal spot tubes, focal spot tuning apparatus 112 can be repositioned, or different focal spot tuning apparatuses can be used, at different positions to utilize the different focal spots of the x-ray tube. Furthermore, many mini-focus tube designs use a severe target angle to produce smaller focal spots. The use of severe target angles can cause distorted focal spot shapes, variability in photon distribution and extensive heal effect causing a variability in x-ray flux output as well as variability in spatial resolution in different directions. Focal spot tuning apparatus 112 may enable use of tube designs with less severe target angles to produce focal spots ranging from conventional to micro-focus, while producing more uniform beam shapes and more homogenous x-ray photon distributions. For example, focal spot tuning apparatus 112 may enable mini- or micro-focus size effective focal spots with a target angle typical of conventionally sized focal spots (e.g., 30 degrees).

Focal spot tuning apparatus 112 may be manufactured in a variety of ways. For example, focal spot tuning apparatus 112 may be manufactured using 3D printing, powder metal, micro machining, etching, electroforming, laser drilling, powder formation, and other manufacturing methods. In various examples, focal spot tuning apparatus 112 may be manufactured as a single component or may be manufactured in multiple sections and assembled as defined by a manufacturing method.

As noted above, some conventional configurations of x-ray tubes reduce the focal spots by adjusting the angle of a target (e.g., anode 208). Adjusting the angle of the target may produce a negative side effect whereby the focal spot across the target is not uniform. For example, the focal spot may be non-uniform in shape. For instance, the focal spot may be oval shaped or have wing-shaped extensions from the corners of an otherwise square shaped focal spot. In another example, the focal spot may be non-uniform in intensity. For instance, more radiation may be output by some parts of the focal spot than other parts of the focal spot. A non-uniform focal spot or other influence may produce, within a radiograph, an unsharpness condition that varies from the anode side to the cathode side of the target. In accordance with a technique of this disclosure, the channel structure size in focal spot tuning apparatus 112 may vary proportionately to offset the variation of the focal spot. Thus, column structure 214 (i.e., inter-channel structures) may define channels 216 such that diameters of channels 216 narrow from one side (e.g., a side closer to cathode 206) of focal spot tuning apparatus 112 to an opposite side (e.g., a side closer to anode 208) of focal spot tuning apparatus 112. For example, channels closer to cathode 206 may be smaller than channels closer to anode 208. This may serve to even out the distribution of photons passing through focal spot tuning apparatus 112. In this way, the inter-channel structures define the channels such that diameters of the channels vary to compensate for an influence (e.g., non-uniformity) known to cause a varying of an unsharpness condition from the focal spot. Varying the channel structure size may also be accomplished by utilizing varying thickness of focal spot tuning apparatus 112 to offset the focal spot variation. For example, channels closer to cathode 206 may be longer than channels closer to anode 208. Thus, photons are less likely to successfully pass through the channels closer to cathode 206. This may help equalize the focal spot across the entire focal spot producing a uniform amount of unsharpness across a radiograph, or an equal spatial resolution across the radiograph. In either of these examples, motion system 232 may oscillate focal spot tuning apparatus 112 to prevent photons emerging from the effective focal spot at certain angles from always being blocked by focal spot tuning apparatus 112.

Figure 3:
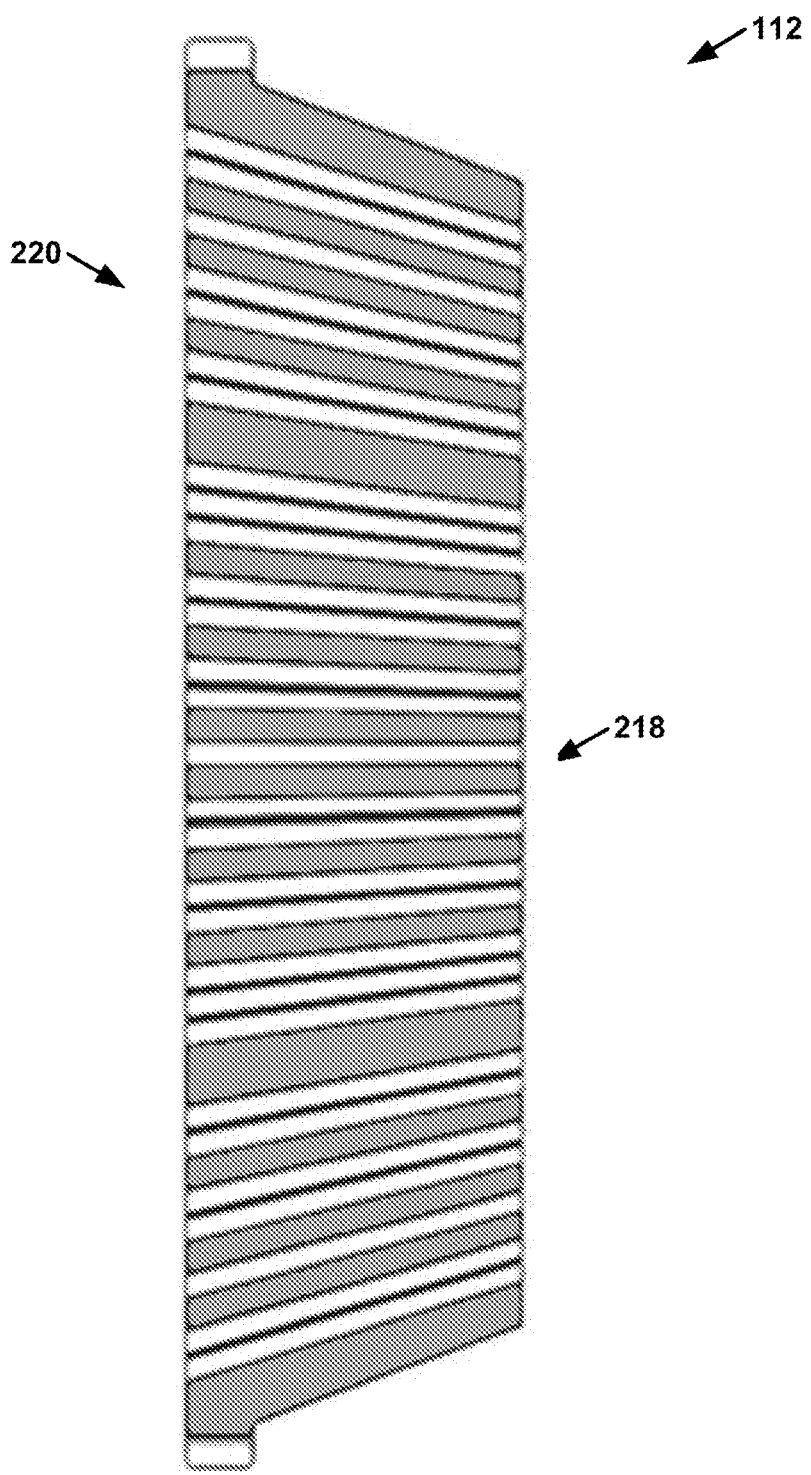
FIG. 3 is a conceptual diagram illustrating an example section view of the focal spot tuning apparatus, in accordance with a technique of this disclosure.

FIG. 3 is a conceptual diagram illustrating an example section view of focal spot tuning apparatus 112, in accordance with a technique of this disclosure. In the example of FIG. 3, channels 216 are shown as white areas extending from source-side surface 218 to object-side surface 220 of focal spot tuning apparatus 112. Furthermore, in the example of FIG. 3, column structures 214 are shown as shaded areas.

Figure 4:
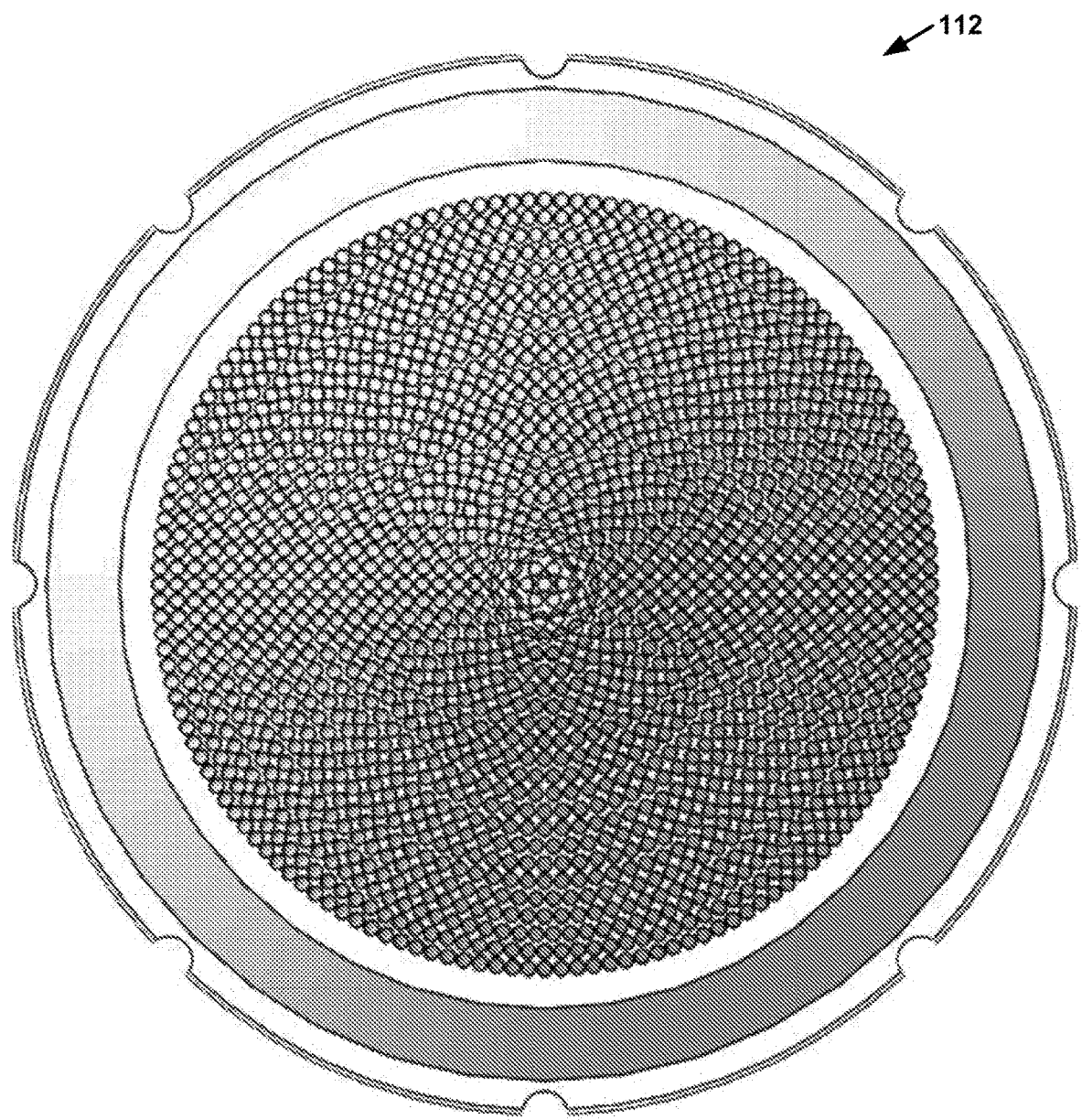
FIG. 4 is a conceptual diagram illustrating an example front view of the focal spot tuning apparatus, in accordance with a technique of this disclosure.

FIG. 4 is a conceptual diagram illustrating an example front view of focal spot tuning apparatus 112, in accordance with a technique of this disclosure. In other words, FIG. 4 illustrates an example of focal spot tuning apparatus 112 showing source-side surface 218. In the example of FIG. 4, the openings of channels 216 are shown as small circles.

Figure 5:
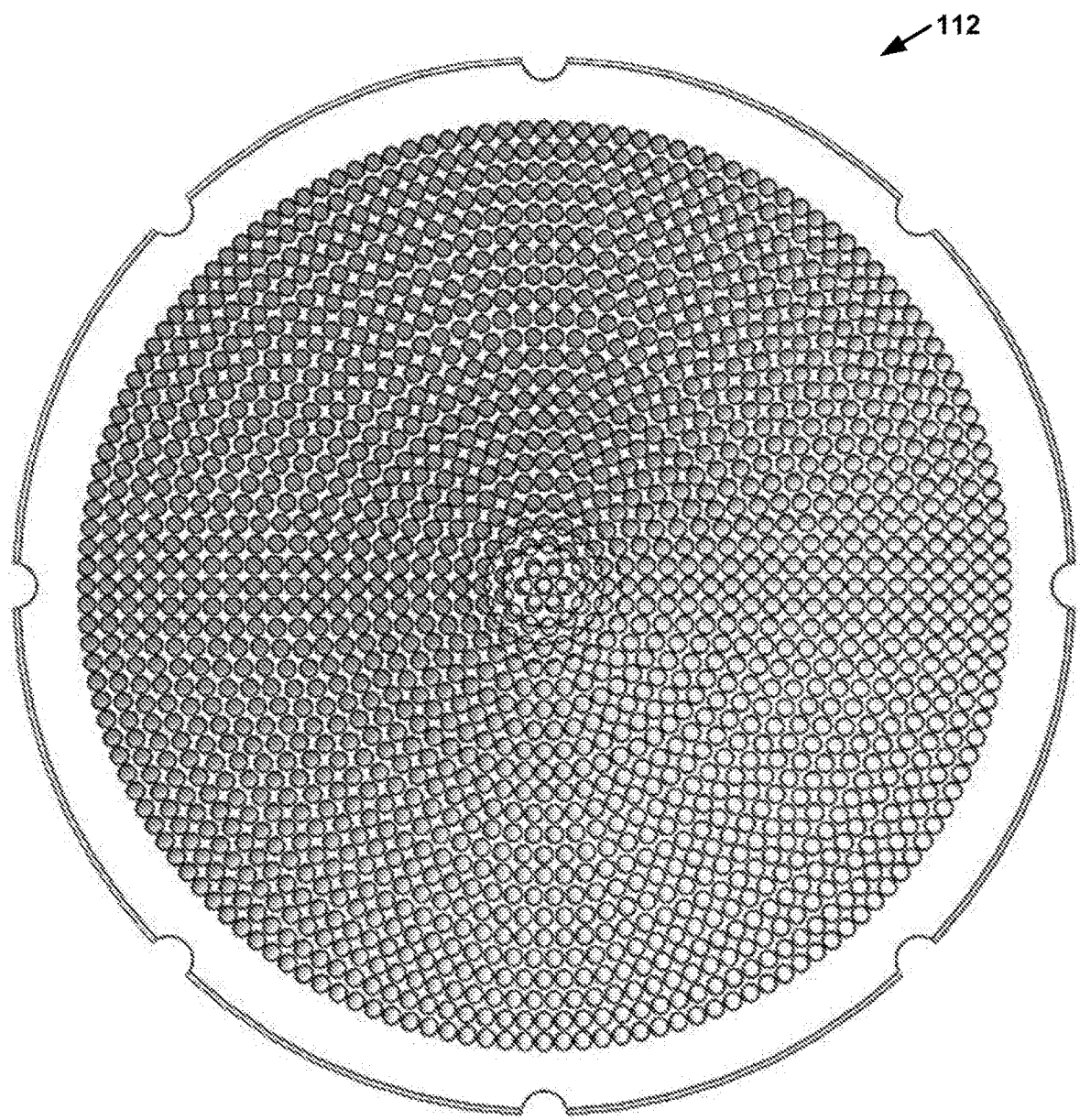
FIG. 5 is a conceptual diagram illustrating an example rear view of the focal spot tuning apparatus, in accordance with a technique of this disclosure.

FIG. 5 is a conceptual diagram illustrating an example rear view of focal spot tuning apparatus 112, in accordance with a technique of this disclosure. In other words, FIG. 5 illustrates an example of focal spot tuning apparatus 112 showing object-side surface 220. In the example of FIG. 5, the openings of channels 216 are shown as small circles. Note that the openings of channels 216 are spread over a wider area than in FIG. 4 because of the spreading paths of channels 216 from source-side surface 218 to object-side surface 220.

Figure 6:
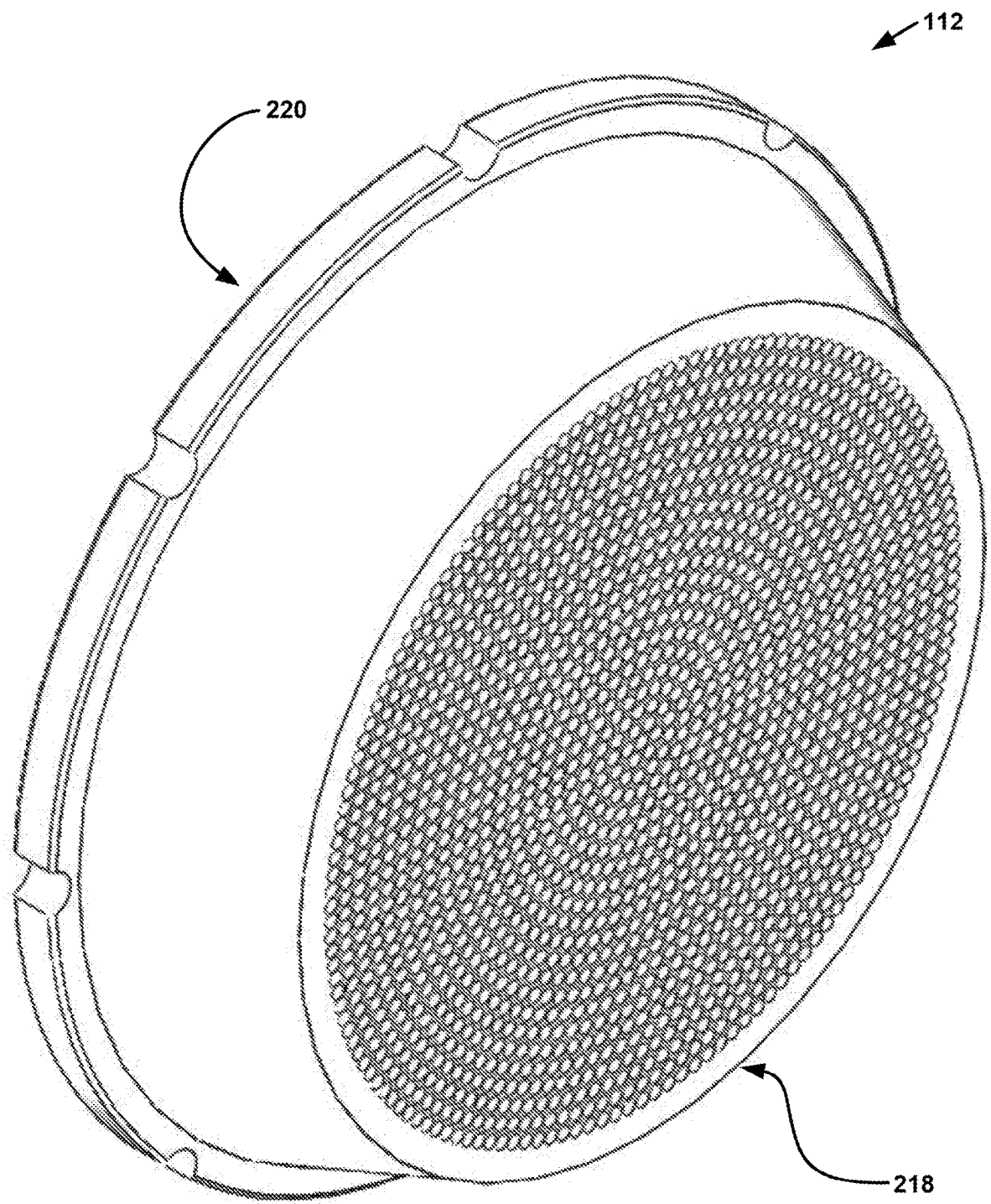
FIG. 6 is a conceptual diagram illustrating an example perspective view of the focal spot tuning apparatus, in accordance with a technique of this disclosure.

FIG. 6 is a conceptual diagram illustrating an example perspective view of focal spot tuning apparatus 112, in accordance with a technique of this disclosure. In the example of FIG. 6, focal spot tuning apparatus 112 increases in diameter from source-side surface 218 to object-side surface 220. In the example of FIG. 6, the openings of channels 216 are shown as small circles on source-side surface 218. Although focal spot tuning apparatus 112 is shown in the example of FIG. 6 as having a flat object-side surface 220 and a flat source-side surface 218, object-side surface 220 and/or source-side surface 218 may be convex or concave. Thus, the following may apply with respect to focal spot tuning apparatus: at least one of a first surface (e.g., source-side surface 218) of focal spot tuning apparatus 112 is concave or a second surface (e.g., object-side surface 220) of focal spot tuning apparatus 112 is convex. The aforementioned concave and convex surface of focal spot tuning apparatus 112 allows for equal distance of travel through the plurality of channels 216 in focal spot tuning apparatus 112.

Figure 7:
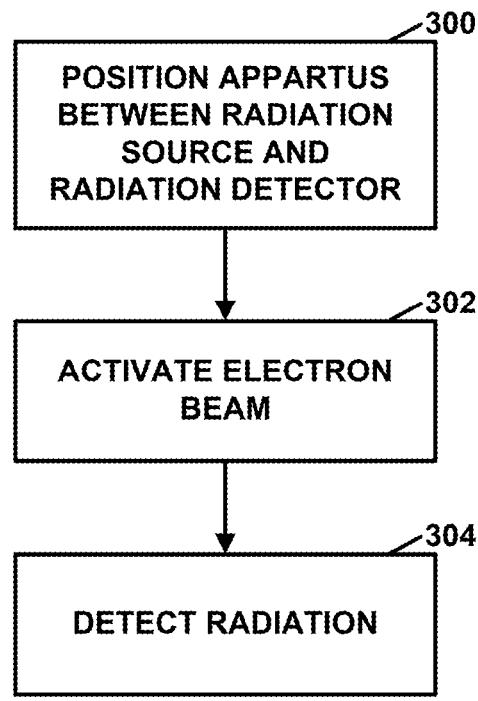
FIG. 7 is a flowchart illustrating an example operation of tuning an effective focal spot of a radiation source, in accordance with a technique of this disclosure.

FIG. 7 is a flowchart illustrating an example operation of tuning an effective focal spot of a radiation source, in accordance with a technique of this disclosure. In the example of FIG. 7, a user or device may position an apparatus (e.g., focal point tuning apparatus 112) between the radiation source and a radiation detector (300). The apparatus may comprise a plurality of inter-channel structures defining a plurality of channels passing through the apparatus from a first surface to a second surface. The inter-channel structures comprise a first substance. The channels contain a second substance. In this example, the first substance attenuates radiation more than the second substance and the inter-channel structures define the channels such that lines passing through the channels converge. For instance, conceptual lines passing through each of the channels may converge at the same point in space. Furthermore, the device (e.g., x-ray source 102) may activate an electron beam that travels across a gap between a cathode (e.g., cathode 206) and an anode (e.g., anode 208) (302). For example, the device may apply a voltage across the gap between the cathode and the anode such that the electron beam travels across the gap from the cathode to the anode. In this example, an area covered by a projection of the lines through the channels is smaller than a focal spot of the electron beam on the anode. In some examples, such as when a gamma ray source is used, action (302) may be omitted. Furthermore, in the example of FIG. 7, a radiation detector (e.g., x-ray detector 104 (FIG. 1)) may detect radiation that has passed through the channels (304). The radiation detector may detect the radiation in the manner described in examples elsewhere in this disclosure.

Figure 8:
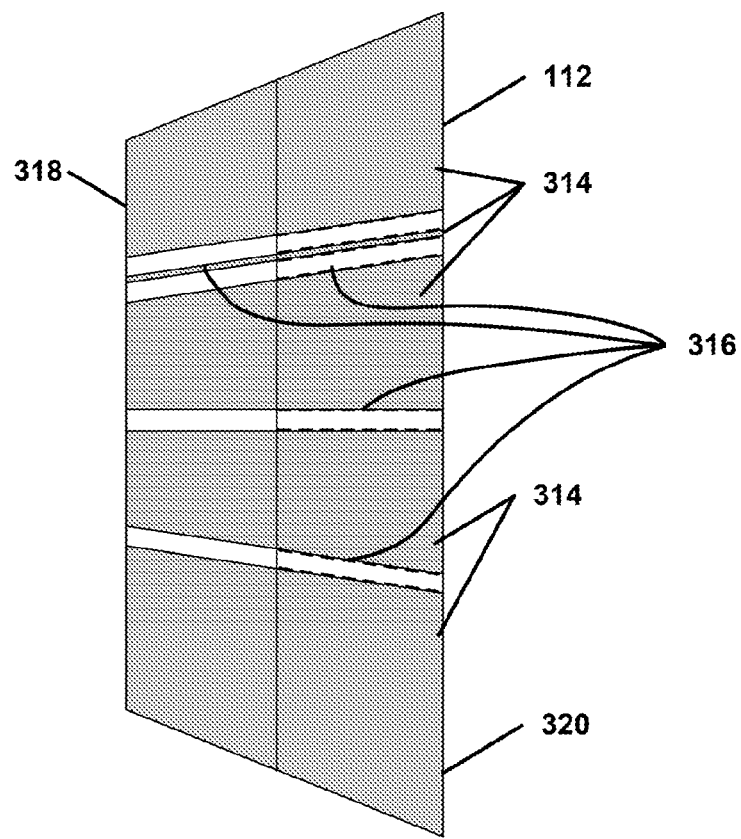
FIG. 8 is a diagram illustrating an example of a focal spot tuning apparatus that has a stacked combination of rough and smooth column surfaces, in accordance with a technique of this disclosure.

FIG. 8 is a diagram illustrating an example of focal spot tuning apparatus 112 that has a stacked combination of rough and smooth column surfaces, in accordance with a technique of this disclosure. In the example of FIG. 8, focal spot tuning apparatus 112 comprises a set of column structures 314. Column structures 314 define channels 316 through focal spot tuning apparatus 112 from a source-side surface 318 of focal spot tuning apparatus 112 to an object-side surface 320 of focal spot tuning apparatus 112.

In some examples, a surface finish of channels 316 may influence the scattering and attenuation of photons. For instance, a smooth surface may allow photon refraction resulting in a higher photon count on the detector side. A rough surface may attenuate additional photons resulting in a lower photon count on the detector side. A stacked combination of both rough and smooth column surfaces within the apparatus may produce enhanced results. Thus, as shown in the example of FIG. 8, using dashed lines, the surfaces of channels 316 closer to source-side surface 318 are relatively smooth. The surfaces of channels 316 closer to object-side surface 320 are rough, relative to the surfaces of channels closer to source-side surface 318. Thus, in the example of FIG. 8, for at least one of channels 316, column structures 314 (i.e., inter-channel structures) define the channel such that a first segment of an inner surface of the channel is smoother than a second segment of the inner surface of the channel.

Figure 9:
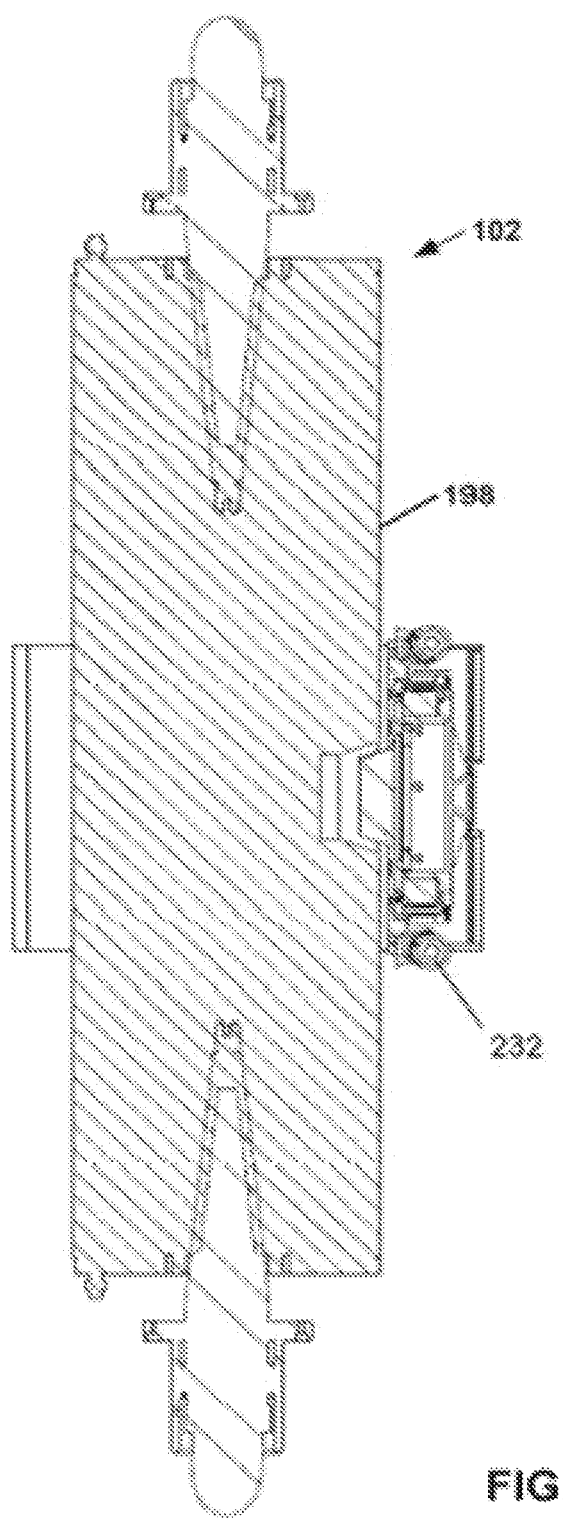
FIG. 9 is a diagram illustrating an example cross sectional view of an x-ray inspection apparatus, in accordance with one or more techniques of this disclosure.

FIG. 9 is a diagram illustrating an example cross sectional view of x-ray source 102, in accordance with one or more techniques of this disclosure. As shown in the example of FIG. 9, x-ray source 102 includes housing 198 and motion system 232. As previously discussed, motion system 232 may be configured to move focal spot tuning apparatus 112 such that column structures 214 do not continuously cast shadows at the same locations on x-ray detector 104. Additionally, motion system 232 may be configured to correctly position focal spot tuning apparatus 112 for a desired effective focal spot size.

Figure 10:
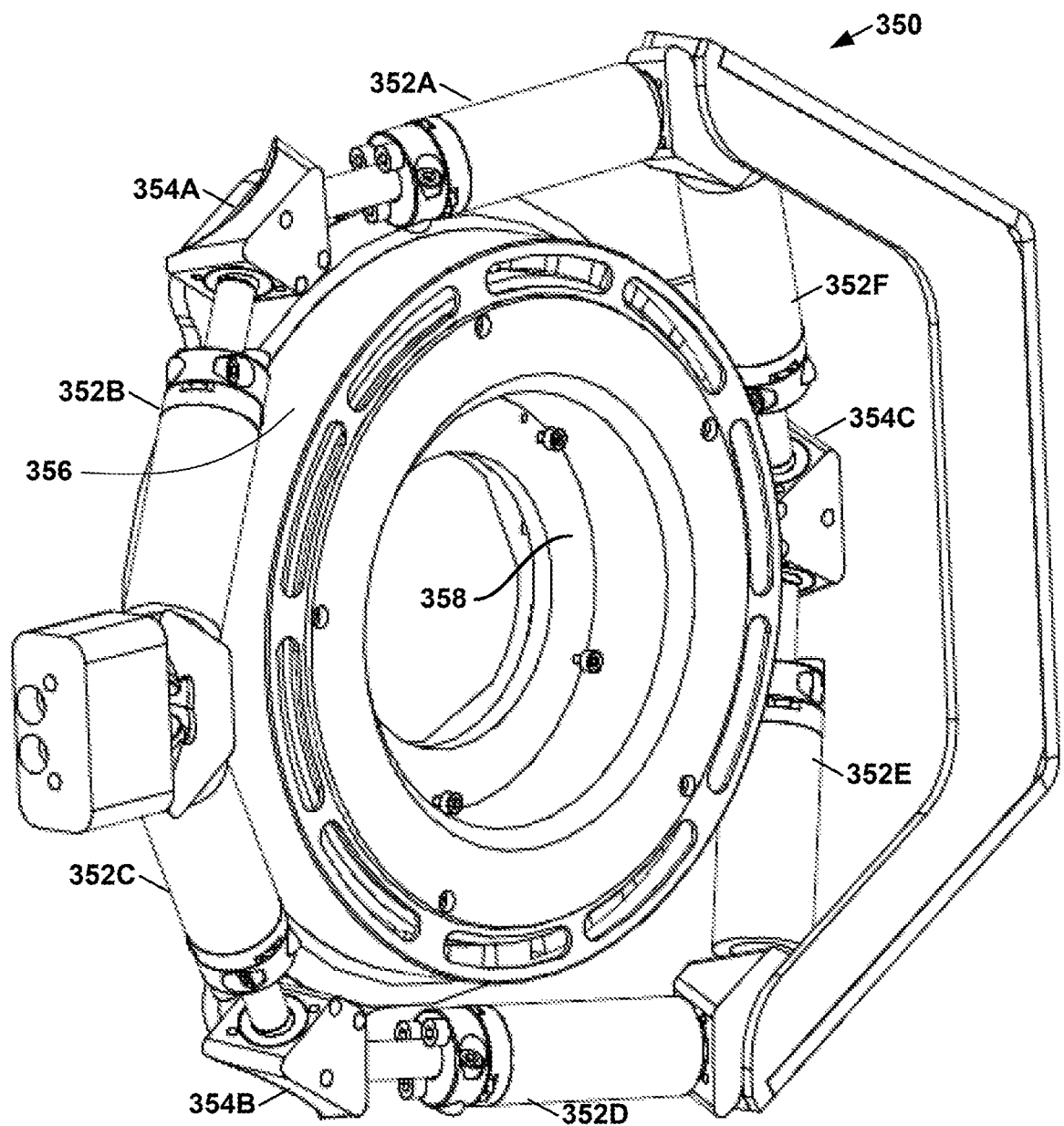
FIG. 10 is a diagram illustrating an example focal spot tuning apparatus adjustment mechanism, in accordance with one or more techniques of this disclosure.

FIG. 10 is a diagram illustrating an example focal spot tuning apparatus adjustment mechanism 350, in accordance with one or more techniques of this disclosure. In the example of FIG. 10, mechanism 350 includes six actuators 352A-352F (collectively, "actuators 352"). Pistons of actuators 352 are coupled to joint members 354A-354C (collectively, "joint members 354") of mechanism 350. Each of joint member 354 may be coupled to a collar member 356 of mechanism 350. Although not shown in the example of FIG. 10, a focal point tuning apparatus (e.g., focal point tuning apparatus 112) may be mounted to an inner ring 358 of collar member 356.

Pistons of actuators 352 may extend or retract to move joint members 354 and hence collar member 356. Thus, movement of the pistons of actuators 352 may move a focal spot tuning apparatus mounted to collar member 356. For instance, extension or retraction of the pistons of actuators 352A and 352D may move collar member 356 horizontally. Concurrent extension or retraction of the pistons of actuators 352B, 352C, 352E, and 352F may move collar member 356 toward or away from a focal spot. Extension of the pistons of actuators 352B and 352F accompanied by retraction of the pistons of actuators 352C and 352E may move collar member 356 downward vertically. Extension of the pistons of actuators 352C and 352E accompanied by retraction of the pistons of actuators 352B and 352F may move collar member 356 upward vertically. In this way, actuators 352 may to adjust the position of focal spot tuning apparatus 112 in as many as 6 degrees of freedom.

A closed loop control system, such as image processing system 110 (FIG. 1) may be used to control the movement of focal spot tuning apparatus 112 to ensure correct positioning of focal spot tuning apparatus 112. For example, the closed loop control system may output signals to mechanism 350 to position focal spot tuning apparatus 112 at a position relatively distant from anode 208. Furthermore, the control system may determine flux of x-rays passing through focal spot tuning apparatus 112 at this position. In this example, the control system may then output signals to mechanism 350 to move focal spot tuning apparatus 112 closer to anode 208. The control system may then determine the flux again. In this example, the flux may continue to increase as focal spot tuning apparatus 112 gets closer to anode 208 until focal spot tuning apparatus 112 gets too close to anode 208. The control system may then step focal spot tuning apparatus 112 back to the position associated with the maximum detected flux. The control system may repeat this process for vertical and horizontal directions. In this way, the control system may perform an automated process of positioning focal spot tuning apparatus 112. After focal spot tuning apparatus 112 is correctly positioned, focal spot tuning apparatus 112 may remain locked in position for use. In some examples, the alignment can be done at a bench-top station using light (instead of x-rays) and a sufficiently accurate control system, either open or closed. In an example of an open control system, a human operator may make adjustments.

In some examples, focal spot tuning apparatus 112 may be removed and reinserted in collar member 356 while collar member 356 remains at a fixed position. Thus, different focal spot tuning apparatuses may be substituted while collar member 356 remains at the fixed position. For instance, different focal spot tuning apparatuses may be substituted to achieve different effective focal spot sizes.

Figure 11:
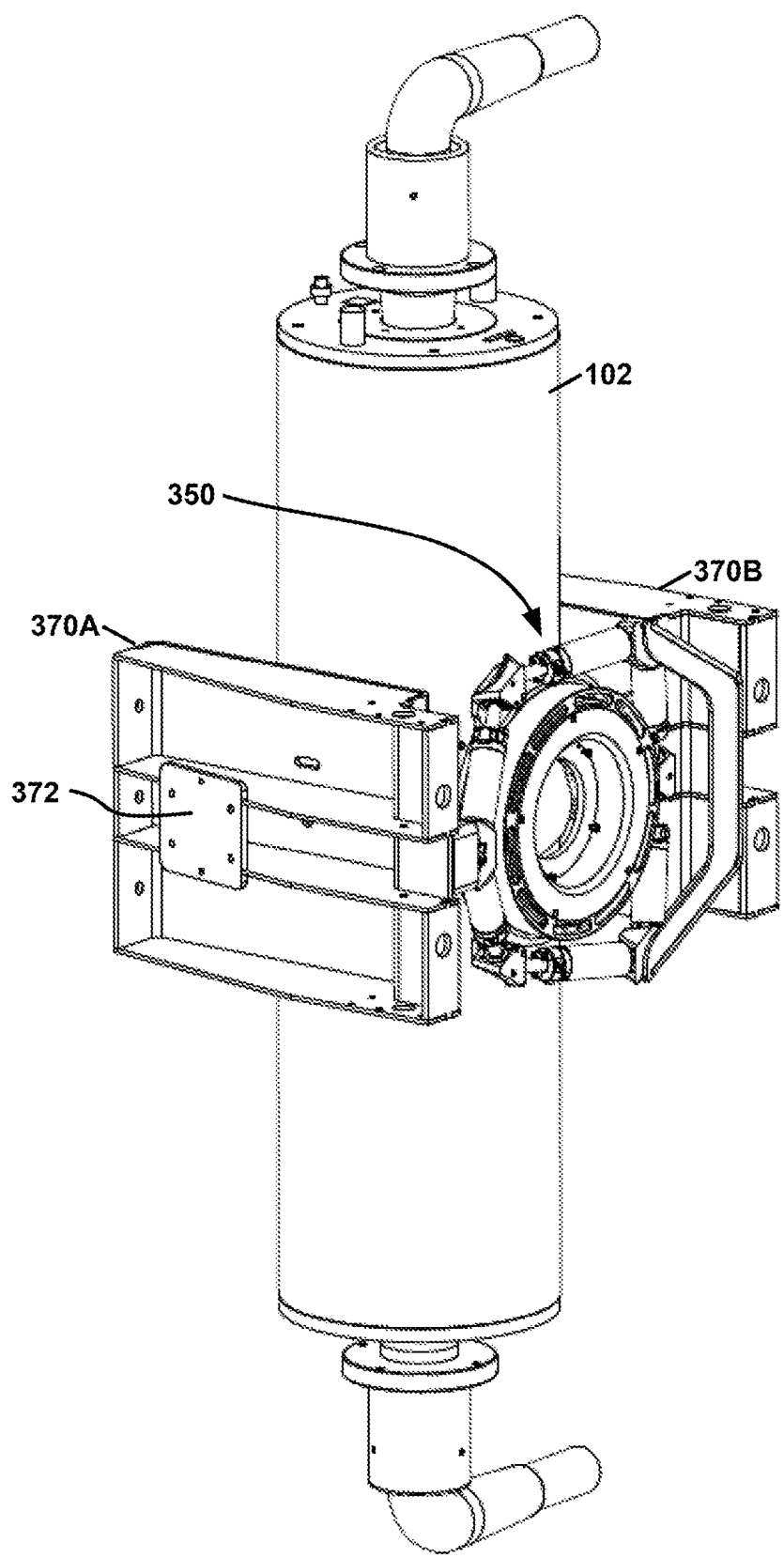
FIG. 11 is a diagram illustrating an example view of a focal spot tuning apparatus adjustment mechanism coupled to an x-ray source, in accordance with one or more techniques of this disclosure.

FIG. 11 is a diagram illustrating an example view of focal spot tuning apparatus adjustment mechanism 350 coupled to x-ray source 102, in accordance with one or more techniques of this disclosure. In the example of FIG. 11, mechanism 350 is coupled to brackets 370A, 370B (collectively, "brackets 370"). In some examples, brackets 370 are coupled to x-ray source 102. In some examples, brackets 370 are not directly coupled to x-ray source 102, but rather may be coupled to another structure (not shown) such that brackets 370 maintain a consistent position relative to x-ray source 102. For instance, a plate 372 coupled to bracket 370A may be used to mount bracket 370A to such a structure.

FIG. 12 is a conceptual diagram illustrating an example profile view of a focal spot tuning apparatus 112, in accordance with one or more techniques of this disclosure. As illustrated in the example of FIG. 12, focal spot tuning apparatus 112 has a concave inner surface 400 and a convex outer surface 402. As shown in FIG. 13, inner surface 400 is concave in 3 dimensions, such that inner surface 400 is bowl shaped. Likewise, as shown in FIG. 13, outer surface 402 is convex in 3 dimensions, such that outer surface 402 is dome shaped.

In this way, the lengths of channels through focal spot tuning apparatus 112 may be the same for x-rays passing through focal spot tuning apparatus 112 at different angles. In other words, all of the channels may have equal length. In contrast, note that in the example of FIG. 3, the channels for higher angles (i.e., further from the center) are longer than the channels for lower angles (i.e., closer to the center). In the example of FIG. 12 and FIG. 13, equalizing channel lengths may help to equalize the number of photons passing through focal spot tuning apparatus at various angles, potentially resulting in a more equal distribution of photons emerging from the outer surface 402 of focal spot tuning apparatus 112.

Figure 14:
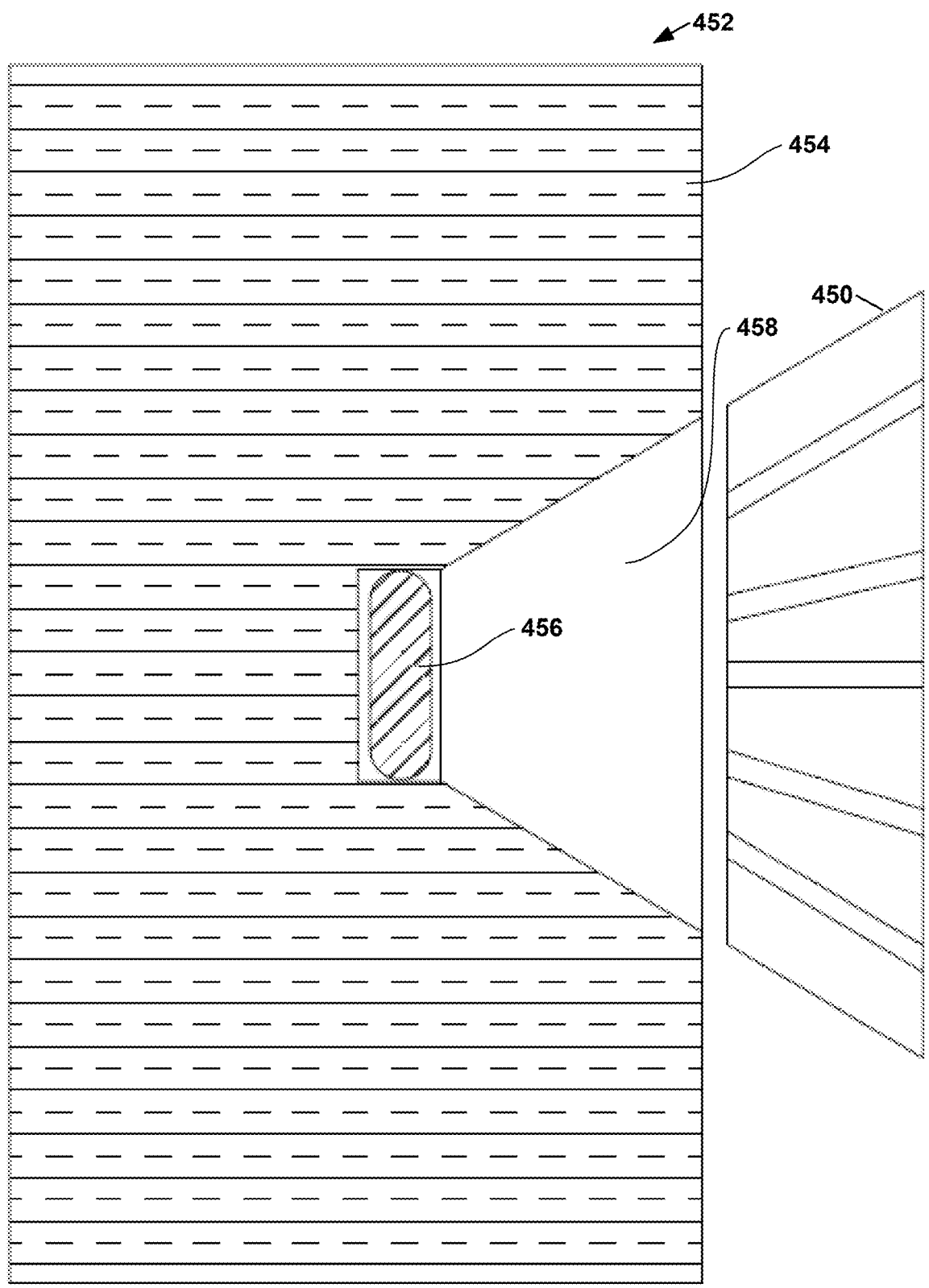
FIG. 14 is an example cross-sectional view of a focal spot tuning apparatus used with a gamma ray source, in accordance with one or more techniques of this disclosure.

FIG. 14 is an example cross-sectional view of a focal spot tuning apparatus 450 used with a gamma ray source 452, in accordance with one or more techniques of this disclosure. In the example of FIG. 14, gamma ray source 452 comprises a radiation shield 454 and a gamma radiation source 456. Gamma radiation source 456 may comprise radioactive material, such as iridium-192. Furthermore, a cavity 458 is defined in radiation shield 454. In the example of FIG. 14, cavity 458 has the shape of a truncated cone. Gamma radiation source 456 is positioned at the base of cavity 458. Focal spot tuning apparatus 450 is positioned at the outer rim of cavity 458 or more proximate to gamma radiation source 456 within the cavity. As with focal spot tuning apparatus 112 described elsewhere in this disclosure, channels are defined in focal spot tuning apparatus 450. The channels of focal spot tuning apparatus 450 are aligned to converge at a spot on or within gamma radiation source 456. Thus, focal spot tuning apparatus 112 may serve to generate a focal spot smaller than the entire surface of gamma radiation source 456. As with mechanisms described elsewhere in this disclosure, the focal spot tuning apparatus 112 may be mounted and adjusted through similar means as shown in FIG. 10.

Figure 15:
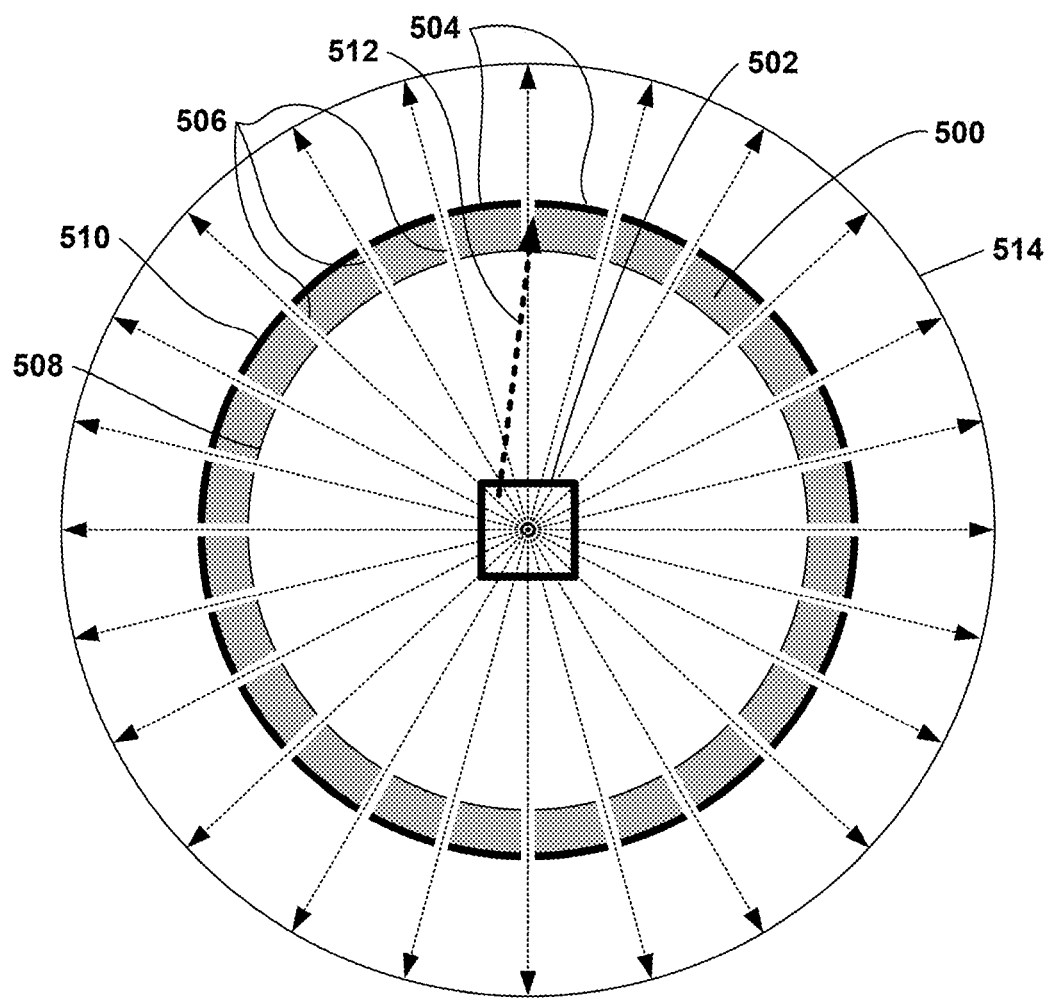
FIG. 15 is a conceptual diagram illustrating another example focal spot tuning apparatus, in accordance with one or more techniques of this disclosure.

FIG. 15 is a conceptual diagram illustrating another example focal spot tuning apparatus 500, in accordance with one or more techniques of this disclosure. In other examples of this disclosure, the radiation passing through focal spot tuning apparatuses was cone-shaped. However, the techniques of this disclosure are not so limited. Rather, radiation passing through focal spot tuning apparatus 500 may be fan-shaped or disc-shaped with angles as great as 360°. In the example of FIG. 15, focal spot tuning apparatus 500 is cylindrical in shape and radiation may pass through focal spot tuning apparatus 500 in a disc-shaped pattern with an angle of 360°. In other examples, angles of 90°, 180°, or any other angle greater than 0° and less than or equal to 360° may be used. A radiation source 502 is disposed at a position along a central axis of the cylinder. Radiation source 502 may comprise a source of gamma rays, such as iridium-192.

Focal spot tuning apparatus 500 comprises a set of column structures 504. Column structures 504 define channels 506 through focal spot tuning apparatus 500. For visual simplicity, reference numbers are provided in FIG. 15 and FIG. 16 for only a small number of column structures 504 and channels 506. Furthermore, for the sake of simplicity, the example of FIG. 15 only shows 24 channels and FIG. 16 only shows a single row of channels. However, column structures 504 may define many more channels. Channels 506 may be filled with a substance having relatively low attenuation for x-rays. For example, channels 506 may contain air or another substance. Column structures 504 may be made of a substance having relatively high attenuation for x-rays. For example, column structures 504 may be made of a high-density material, such as tungsten, lead, lead glass, or tantalum. Because channels 506 contain a low-attenuation substance while column structures 504 comprise a high-attenuation substance, x-rays may be able to pass through channels 506 and may be attenuated by column structures 504.

Column structures 504 define channels 506 such that channels 506 are angled inward from object-side surface 510 to source-side surface 508 such that conceptual lines passing through the centerlines of channels 506 converge at a location at or near a single location within radiation source 502. For instance, the centerlines of channels 506 may converge at or near the center of radiation source 502. As shown by arrow 512, because of the angles of channels 506, radiation emitted by portions of radiation source 502 other than points aligned with the centerlines of channels 506 are less likely to pass through channels 506 from source-side surface 508 to object-side surface 510 without being attenuated by column structures 504. As a result, the effective source of radiation may be smaller than the actual size of radiation source 502. This may improve spatial resolution and contrast sensitivity. As shown in FIG. 15, source-side surface 508 (i.e., a surface facing a point at which the lines passing through channels 506 converge) is cylindrical.

Furthermore, in the example of FIG. 15, a radiation detector 514 may be disposed outside focal spot tuning apparatus 500. In some examples, radiation detector 514 comprises a radiation-sensitive film or an electronic radiation detector. An object to be inspected may be positioned between focal spot tuning apparatus 500 and radiation detector 514. The setup of FIG. 15 may be especially useful when inspecting cylindrical objects, such as pipes and tubes, that may slide between focal spot tuning apparatus 500 and radiation detector 514. For instance, the setup of FIG. 15 may be useful when inspecting a weld in a tube, especially a circumferential weld.

In some examples, a motion system (not shown) may rotate, or otherwise move, focal spot tuning apparatus 500 such that column structures 504 of focal spot tuning apparatus do not continuously cast shadows at the same locations on radiation detector 514.

Figure 16:
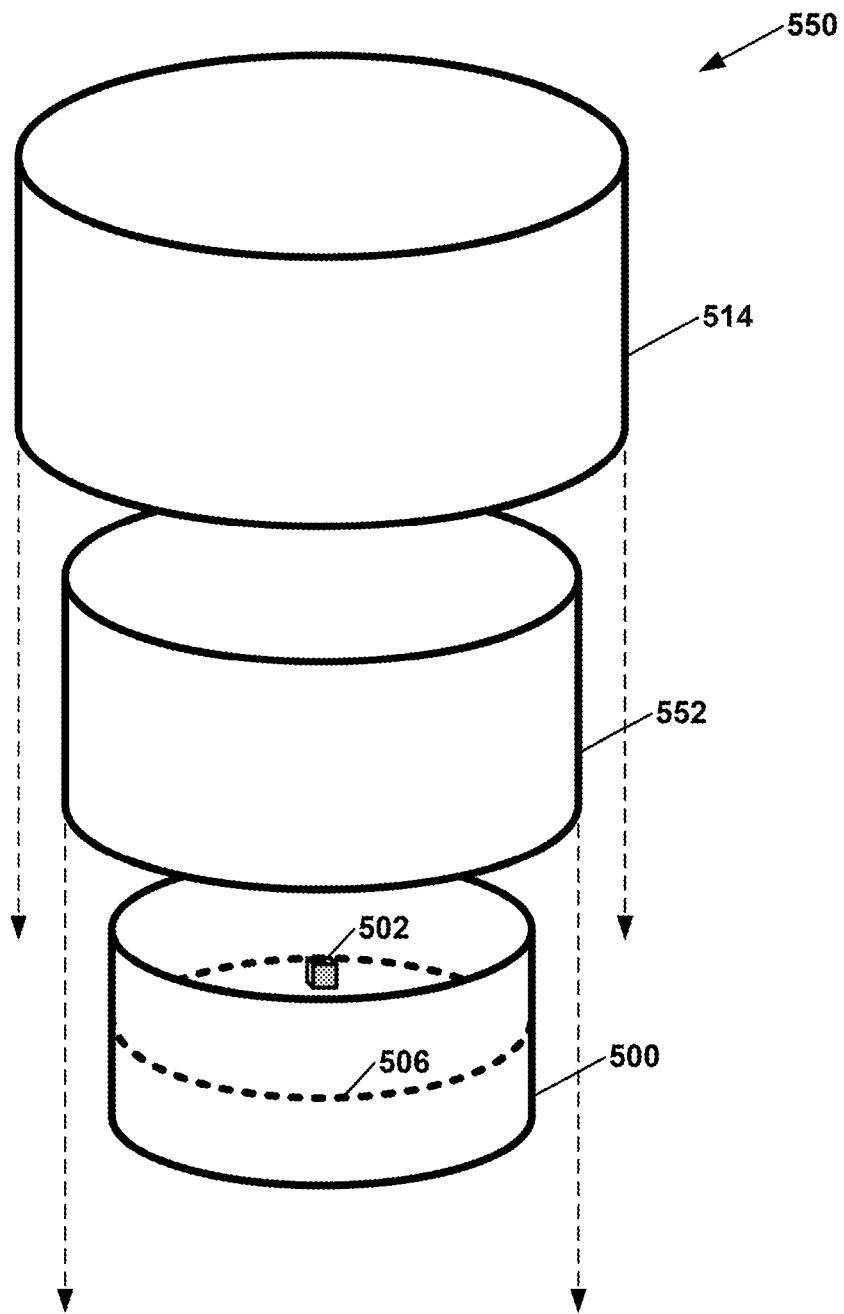
FIG. 16 is an exploded diagram illustrating an example inspection apparatus, in accordance with one or more techniques of this disclosure.

FIG. 16 is an exploded diagram illustrating an example inspection apparatus 550, in accordance with one or more techniques of this disclosure. Inspection apparatus 550 includes focal spot tuning apparatus 500 of FIG. 15. Radiation source 502 is disposed within focal spot tuning apparatus 500. An object 552 to be inspected may be disposed concentrically outside focal spot tuning apparatus 500. Furthermore, for simplicity radiation detector 514 is shown as a single detector disposed concentrically outside object 552. Detectors may be cylindrical, flat, curved, rectangular or any other variation of shape and size. Although not shown in the example of FIG. 16, radiation shielding may be disposed concentrically outside radiation detector 514.

Figure 17:
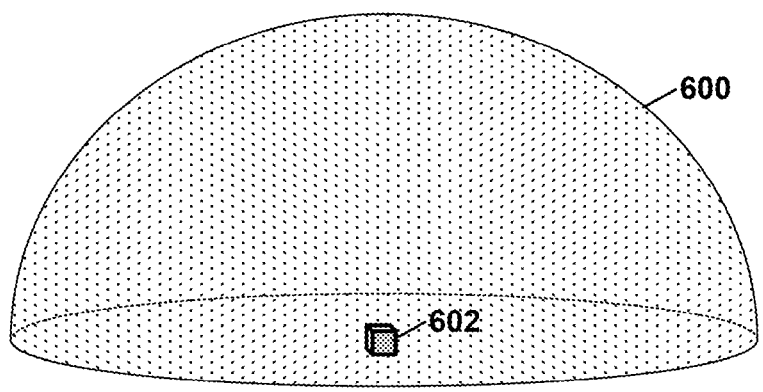
FIG. 17 is a conceptual diagram illustrating a hemispheric focal spot tuning apparatus 600, in accordance with a technique of this disclosure.

FIG. 17 is a conceptual diagram illustrating a hemispheric focal spot tuning apparatus 600, in accordance with a technique of this disclosure. As shown in the example of FIG. 17, focal spot tuning apparatus 600 is hemispherical in shape. In similar examples, focal spot tuning apparatuses may be fully spherical, or may be other spherical sectors, spherical wedges, or spherical segments. Focal spot tuning apparatus 600 may be similar in structure to focal spot tuning apparatus described elsewhere in this disclosure. For instance, channels may be defined in focal spot tuning apparatus 600 such that angles of lines passing through the channels converge at a location within a radiation source 602. This may have a similar effect of providing a smaller effective focal spot.

The following paragraphs describe various examples of techniques of this disclosure.

Example 1

An apparatus for tuning an effective focal spot size of a radiation source, the apparatus comprising: a plurality of inter-channel structures defining a plurality of channels passing through the apparatus from a first surface to a second surface, the inter-channel structures comprising a first substance, the channels containing a second substance, the first substance attenuating radiation more than the second substance, the inter-channel structures defining the channels such that lines passing through the channels converge.

Example 2

The apparatus of example 1, wherein at least one of: the first surface is concave or the second surface is convex.

Example 3

The apparatus of any of examples 1-2, wherein all of the channels are equal length.

Example 4

The apparatus of any of examples 1-3, wherein the inter-channel structures define the channels such that diameters of the channels vary to compensate for non-uniformity of a focal spot of an electron beam.

Example 5

The apparatus of any of examples 1-4, wherein, for at least one of the channels, the inter-channel structures define the channel such that a first segment of an inner surface of the channel is smoother than a second segment of the inner surface of the channel.

Example 6

The apparatus of any of examples 1-5, wherein the inter-channel structures define openings of the channels at a first surface of the apparatus to be wider than openings of the channels at a second surface of the apparatus.

Example 7

The apparatus of any of examples 1-6, wherein the radiation is x-ray radiation or gamma ray radiation.

Example 8

The apparatus of any of examples 1-7, wherein a surface of the apparatus facing a point at which the lines passing through the channels converge is cylindrical.

Example 9

A method of tuning an effective focal spot of a radiation source, the method comprising: positioning an apparatus between the radiation source and a radiation detector, the apparatus comprising a plurality of inter-channel structures defining a plurality of channels passing through the apparatus from a first surface to a second surface, the inter-channel structures comprising a first substance, the channels containing a second substance, the first substance attenuating radiation more than the second substance, the inter-channel structures defining the channels such that lines passing through the channels converge; and detecting, by the radiation detector, radiation that has passed through the channels.

Example 10

The method of example 9, further comprising: activating an electron beam that travels across a gap from a cathode to an anode, wherein an area covered by a projection of the lines through the channels is smaller than a focal spot of the electron beam on the anode.

Example 11

The method of any of examples 9-10, wherein at least one of: the first surface is concave or the second surface is convex.

Example 12

The method of any of examples 9-11, wherein a surface of the apparatus facing a point at which the lines passing through the channels converge is cylindrical.

Example 13

The method of any of examples 9-11, wherein all of the channels are equal length.

Example 14

The method of any of examples 9-13, wherein the inter-channel structures define the channels such that diameters of the channels vary to compensate for non-uniformity of the focal spot.

Example 15

The method of any of examples 9-14, wherein, for at least one of the channels, the inter-channel structures define the channel such that a first segment of an inner surface of the channel is smoother than a second segment of the inner surface of the channel.

Example 16

The method of any of examples 9-15, wherein the inter-channel structures define openings of the channels at a first surface of the apparatus to be wider than openings of the channels at a second surface of the apparatus.

Example 17

The method of any of examples 9-16, wherein the radiation is x-ray radiation or, for any of examples 9 and 11-16, gamma ray radiation.

Example 18

The method of any of examples 9-17, further comprising moving the apparatus toward or away from the anode to adjust a size of the area.

Example 19

The method of any of examples 9-18, further comprising canting or tilting the apparatus to adjust a size of the area.

Example 20

The method of any of examples 9-19, further comprising moving the apparatus such that the inter-channel structures do not continuously cast shadows at locations on a radiation detector.

Example 21

The method of example 20, wherein moving the apparatus comprises at least one of: rotating the apparatus, nutating the apparatus, or oscillating the apparatus.

Example 22

A system comprising: a radiation source configured to deliver radiation towards an object; a radiation detector configured to detect the radiation; and an apparatus for tuning an effective focal spot size of the radiation source, the apparatus comprising: a plurality of inter-channel structures defining a plurality of channels passing through the apparatus from a first surface to a second surface, wherein the inter-channel structures comprise a first substance, the channels include a second substance, the first substance attenuates the radiation more than the second substance, and the inter-channel structures define the channels such that lines passing through the channels converge.

Example 23

The system of example 22, wherein at least one of: the first surface is concave or the second surface is convex.

Example 24

The system of any of examples 22-23, wherein a surface of the apparatus facing a point at which the lines passing through the channels converge is cylindrical.

Example 25

The system of any of examples 22-24, wherein all of the channels are equal length.

Example 26

The system of any of examples 22-25, wherein the inter-channel structures define the channels such that diameters of the channels vary to compensate for non-uniformity of the focal spot.

Example 27

The system of any of examples 22-26, wherein, for at least one of the channels, the inter-channel structures define the channel such that a first segment of an inner surface of the channel is smoother than a second segment of the inner surface of the channel.

Example 28

The system of any of examples 22-27, wherein the inter-channel structures define openings of the channels at a first surface of the apparatus to be wider than openings of the channels at a second surface of the apparatus.

Example 29

The system of any of examples 22-27, wherein the radiation is x-ray radiation or, for any of examples 22 and 23-27, gamma ray radiation.

Example 30

The system of any of examples 22-29, further comprising a motion system configured to move the apparatus toward or away from an anode of the radiation source to adjust the effective focal spot size.

Example 31

The system of any of examples 22-30, further comprising a motion system configured to canting or tilting the apparatus to adjust the effective focal spot size.

Example 32

The system of any of examples 22-31, further comprising a motion system configured to move the apparatus such that the inter-channel structures do not continuously cast shadows at locations on a radiation detector.

Example 33

The system of example 32, wherein the motion system is configured to rotate the apparatus, nutate the apparatus, or oscillate the apparatus.

Example 34

The system of any of examples 22-33, wherein the radiation source comprises a cathode and an anode, wherein during operation of the system, an electron beam travels across a gap from the cathode to the anode, wherein the effective focal spot size is smaller than a focal spot of the electron beam on the anode.

Various examples have been described. These and other examples are within the scope of the following claims. For example, although much of this disclosure refers to x-rays, the discussion of x-rays may apply equally to other types of radiation, such as gamma rays.

The invention claimed is:

1. A method of tuning an effective focal spot of a radiation source, the method comprising:
   positioning an apparatus between the radiation source and a radiation detector, the apparatus comprising a plurality of inter-channel structures defining a plurality of channels passing through the apparatus from a first surface to a second surface, the inter-channel structures comprising a first substance, the channels containing a second substance, the first substance attenuating radiation more than the second substance, the inter-channel structures defining the channels such that lines passing through the channels converge;
   moving the apparatus such that the inter-channel structures do not continuously cast shadows at locations on the radiation detector, wherein moving the apparatus comprises nutating the apparatus; and
   detecting, by the radiation detector, radiation that has passed through the channels.

2. The method of claim 1, further comprising:
   activating an electron beam that travels across a gap from a cathode to an anode, wherein an area covered by a projection of the lines through the channels is smaller than a focal spot of the electron beam on the anode.

3. The method of claim 1, wherein at least one of: the first surface is concave or the second surface is convex.

4. The method of claim 1, wherein a source-side surface of the apparatus facing a point at which the lines passing through the channels converge is cylindrical.

5. The method of claim 1, wherein all of the channels are equal length.

6. The method of claim 1, wherein the inter-channel structures define the channels such that a first diameter of a first channel of the plurality of channels differs from a second diameter of a second channel of the plurality of channels to compensate for non-uniformity of the focal spot.

7. The method of claim 1, wherein, for at least one of the channels, the inter-channel structures define the channel such that a first segment of an inner surface of the channel is smoother than a second segment of the inner surface of the channel.

8. The method of claim 1, wherein the inter-channel structures define openings of the channels at a first surface of the apparatus to be wider than openings of the channels at a second surface of the apparatus.

9. The method of claim 1, wherein the radiation is x-ray radiation or gamma ray radiation.

10. The method of claim 2, further comprising moving the apparatus toward or away from the anode to adjust a size of the area.

11. The method of claim 2, further comprising canting or tilting the apparatus to adjust a size of the area.

12. A system comprising:
   a radiation source configured to deliver radiation towards an object;
   a radiation detector configured to detect the radiation; and
   an apparatus for tuning an effective focal spot size of the radiation source, the apparatus comprising:
      a plurality of inter-channel structures defining a plurality of channels passing through the apparatus from a first surface to a second surface, wherein the inter-channel structures comprise a first substance, the channels include a second substance, the first substance attenuates the radiation more than the second substance, and the inter-channel structures define the channels such that lines passing through the channels converge; and
      a motion system configured to move the apparatus such that the inter-channel structures do not continuously cast shadows at locations on the radiation detector, wherein the motion system is configured to nutate the apparatus.

13. The system of claim 12, wherein at least one of: the first surface is concave or the second surface is convex.

14. The system of claim 12, wherein a source-side surface of the apparatus facing a point at which the lines passing through the channels converge is cylindrical.

15. The system of claim 12, wherein all of the channels are equal length.

16. The system of claim 12, wherein the inter-channel structures define the channels such that a first diameter of a first channel of the plurality of channels differs from a second diameter of a second channel of the plurality of channels to compensate for non-uniformity of the focal spot.

17. The system of claim 12, wherein, for at least one of the channels, the inter-channel structures define the channel such that a first segment of an inner surface of the channel is smoother than a second segment of the inner surface of the channel.

18. The system of claim 12, wherein the inter-channel structures define openings of the channels at a first surface of the apparatus to be wider than openings of the channels at a second surface of the apparatus.

19. The system of claim 12, wherein the radiation is x-ray radiation or gamma ray radiation.

20. The system of claim 12, wherein the motion system is further configured to move the apparatus toward or away from an anode of the radiation source to adjust the effective focal spot size.

21. The system of claim 12, wherein the motion system is further configured to cant or tilt the apparatus to adjust the effective focal spot size.

22. The system of claim 12, wherein the radiation source comprises a cathode and an anode, wherein during operation of the system, an electron beam travels across a gap from the cathode to the anode, wherein the effective focal spot size is smaller than a focal spot of the electron beam on the anode.

* * * * *